US009820775B2

(12) United States Patent
Singh et al.

(10) Patent No.: US 9,820,775 B2
(45) Date of Patent: *Nov. 21, 2017

(54) BONE TRANSPORT EXTERNAL FIXATION FRAME

(71) Applicant: Stryker European Holdings I, LLC, Kalamazoo, MI (US)

(72) Inventors: Manoj Kumar Singh, Mahwah, NJ (US); Yves Stephane Crozet, Ramsey, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/792,856

(22) Filed: Jul. 7, 2015

(65) Prior Publication Data
US 2015/0305777 A1    Oct. 29, 2015

Related U.S. Application Data

(63) Continuation of application No. 13/592,832, filed on Aug. 23, 2012, now Pat. No. 9,101,398.

(51) Int. Cl.
*A61B 17/56* (2006.01)
*A61B 17/62* (2006.01)
*A61B 17/66* (2006.01)

(52) U.S. Cl.
CPC .............. *A61B 17/62* (2013.01); *A61B 17/66* (2013.01)

(58) Field of Classification Search
CPC ..... A61B 17/62; A61B 17/66; A61B 17/6466; A61B 17/6416; A61B 7/6475;
(Continued)

(56) References Cited

U.S. PATENT DOCUMENTS 6,214 A    3/1849  Yerger
2,035,952 A    3/1936  Ettinger
(Continued)

FOREIGN PATENT DOCUMENTS

CH    596826 A5    3/1978
DE    4421223 A1    12/1995
(Continued)

OTHER PUBLICATIONS

Basic Ilizarov Techniques, Techniques in Orthopaedics, vol. 5, No. 4, pp. 55-59, Dec. 1990.
(Continued)

*Primary Examiner* — Eduardo C Robert
*Assistant Examiner* — Tara R Carter
(74) *Attorney, Agent, or Firm* — Lerner, David, Littenberg, Krumholz & Mentlik, LLP

(57) ABSTRACT

Disclosed herein are systems and methods for manipulating the orientation of a plurality of bone fragments with respect to one another. A bone transport frame including first and second rings, a plurality of elongate struts, and a plurality of ring transport assemblies for orienting a first bone segment with respect to a second bone segment is disclosed. A third ring may be included in the bone transport frame for orienting a third bone segment with respect to the first and second bone segments. Manipulation of an adjustable member of the bone transport frame can transport a ring in either a proximal or distal direction with respect to other rings of the frame. Manipulation of another adjustable member of the bone transport frame can translate a central axis of one of the rings either toward or away from the central axes of the plurality of elongate struts.

18 Claims, 28 Drawing Sheets

(58) Field of Classification Search
CPC .......... A61B 17/7077; A61B 2017/292; A61B 2017/606; A61B 90/14; A61B 17/6491; Y10T 403/32; Y10T 403/7105
USPC .................................................. 606/53–59
See application file for complete search history.

(56) References Cited

U.S. PATENT DOCUMENTS

| | | |
|---|---|---|
| 2,055,024 A | 9/1936 | Bittner |
| 2,291,747 A | 8/1942 | Neuwirth |
| 2,333,033 A | 10/1943 | Mraz |
| 2,391,537 A | 12/1945 | Anderson |
| 2,393,831 A | 1/1946 | Stader |
| 2,406,987 A | 9/1946 | Anderson |
| 2,883,219 A | 4/1959 | Cox |
| 3,691,788 A | 9/1972 | Mazziotti |
| 3,727,610 A | 4/1973 | Riniker |
| 3,863,037 A | 1/1975 | Schindler et al. |
| 3,941,123 A | 3/1976 | Volkov et al. |
| 3,977,397 A | 8/1976 | Kalnberz et al. |
| 3,985,127 A | 10/1976 | Volkov et al. |
| 4,006,740 A | 2/1977 | Volkov et al. |
| 4,100,919 A | 7/1978 | Oganesyan et al. |
| 4,127,119 A | 11/1978 | Kronner |
| 4,185,623 A | 1/1980 | Volkov et al. |
| 4,308,863 A | 1/1982 | Fischer |
| 4,338,927 A | 7/1982 | Volkov et al. |
| 4,365,624 A | 12/1982 | Jaquet |
| 4,403,606 A | 9/1983 | Woo et al. |
| 4,450,834 A | 5/1984 | Fischer |
| 4,520,983 A | 6/1985 | Templeman |
| 4,548,199 A | 10/1985 | Agee |
| 4,554,915 A | 11/1985 | Brumfield |
| 4,611,586 A | 9/1986 | Agee et al. |
| 4,615,338 A | 10/1986 | Ilizarov et al. |
| 4,730,608 A | 3/1988 | Schlein |
| 4,768,524 A | 9/1988 | Hardy |
| 4,784,125 A | 11/1988 | Monticelli et al. |
| 4,819,496 A | 4/1989 | Shelef |
| 4,889,111 A | 12/1989 | Ben-Dov |
| 4,976,582 A | 12/1990 | Clavel |
| 4,978,348 A | 12/1990 | Ilizarov |
| 5,028,180 A | 7/1991 | Sheldon et al. |
| 5,062,844 A * | 11/1991 | Jamison ................ A61B 17/62 606/54 |
| 5,067,954 A | 11/1991 | Ilizarov |
| 5,074,866 A | 12/1991 | Sherman et al. |
| 5,087,258 A | 2/1992 | Schewior |
| 5,112,331 A | 5/1992 | Miletich |
| 5,122,140 A | 6/1992 | Asche et al. |
| 5,160,335 A | 11/1992 | Wagenknecht |
| 5,179,525 A | 1/1993 | Griffis et al. |
| 5,207,676 A | 5/1993 | Canadell et al. |
| 5,275,598 A | 1/1994 | Cook |
| 5,279,176 A | 1/1994 | Tahmasebi et al. |
| 5,301,566 A | 4/1994 | Tahmasebi et al. |
| 5,353,504 A | 10/1994 | Pai |
| 5,358,504 A | 10/1994 | Paley et al. |
| 5,372,597 A | 12/1994 | Hotchkiss et al. |
| 5,391,167 A | 2/1995 | Pong et al. |
| 5,397,322 A | 3/1995 | Campopiano et al. |
| 5,437,666 A | 8/1995 | Tepic et al. |
| 5,451,225 A | 9/1995 | Ross, Jr. et al. |
| 5,466,237 A | 11/1995 | Byrd, III et al. |
| 5,496,319 A | 3/1996 | Allard et al. |
| 5,540,686 A | 7/1996 | Zippel et al. |
| 5,568,993 A | 10/1996 | Potzick |
| 5,630,814 A | 5/1997 | Ross, Jr. et al. |
| 5,658,283 A | 8/1997 | Huebner |
| 5,662,648 A | 9/1997 | Faccioli et al. |
| 5,681,309 A | 10/1997 | Ross, Jr. et al. |
| 5,688,271 A | 11/1997 | Faccioli et al. |
| 5,702,389 A * | 12/1997 | Taylor .................. A61B 17/62 606/56 |
| 5,709,681 A | 1/1998 | Pennig |
| 5,713,897 A | 2/1998 | Goble et al. |
| 5,725,526 A | 3/1998 | Allard et al. |
| 5,725,527 A | 3/1998 | Biedermann et al. |
| 5,728,095 A | 3/1998 | Taylor et al. |
| 5,766,173 A | 6/1998 | Ross, Jr. et al. |
| 5,776,132 A | 7/1998 | Blyakher |
| 5,776,173 A | 7/1998 | Madsen, Jr. et al. |
| 5,788,695 A | 8/1998 | Richardson |
| 5,797,908 A | 8/1998 | Meyers et al. |
| 5,843,081 A | 12/1998 | Richardson |
| 5,846,245 A | 12/1998 | McCarthy et al. |
| 5,863,292 A | 1/1999 | Tosic |
| 5,870,834 A | 2/1999 | Sheldon |
| 5,885,282 A | 3/1999 | Szabo |
| 5,891,143 A | 4/1999 | Taylor et al. |
| 5,897,555 A | 4/1999 | Clyburn et al. |
| 5,919,192 A | 7/1999 | Shouts |
| 5,921,985 A | 7/1999 | Ross, Jr. et al. |
| 5,928,230 A | 7/1999 | Tosic |
| 5,931,837 A | 8/1999 | Marsh et al. |
| 5,968,043 A | 10/1999 | Ross, Jr. et al. |
| 5,971,984 A | 10/1999 | Taylor et al. |
| 5,976,133 A | 11/1999 | Kraus et al. |
| 5,997,537 A | 12/1999 | Walulik |
| 6,007,535 A | 12/1999 | Rayhack et al. |
| 6,010,501 A | 1/2000 | Raskin et al. |
| 6,013,081 A | 1/2000 | Burkinshaw et al. |
| 6,021,579 A | 2/2000 | Schimmels et al. |
| 6,030,386 A | 2/2000 | Taylor et al. |
| 6,036,691 A | 3/2000 | Richardson |
| 6,086,283 A | 7/2000 | Ziegert |
| 6,090,111 A | 7/2000 | Nichols |
| 6,099,217 A | 8/2000 | Wiegand et al. |
| 6,129,727 A | 10/2000 | Austin et al. |
| 6,176,860 B1 | 1/2001 | Howard |
| 6,196,081 B1 | 3/2001 | Yau |
| 6,245,071 B1 | 6/2001 | Pierson |
| 6,277,118 B1 | 8/2001 | Grant et al. |
| 6,328,737 B1 | 12/2001 | Moorcroft et al. |
| 6,342,052 B1 | 1/2002 | Allende |
| 6,342,054 B1 | 1/2002 | Mata |
| 6,355,037 B1 | 3/2002 | Crosslin et al. |
| 6,371,957 B1 | 4/2002 | Amrein et al. |
| 6,391,250 B1 | 5/2002 | Wolfsgruber et al. |
| 6,423,061 B1 | 7/2002 | Bryant |
| 6,428,540 B1 | 8/2002 | Claes et al. |
| 6,491,694 B1 | 12/2002 | Orsak |
| 6,537,275 B2 | 3/2003 | Venturini et al. |
| 6,565,565 B1 | 5/2003 | Yuan et al. |
| 6,565,567 B1 | 5/2003 | Haider |
| 6,610,063 B2 | 8/2003 | Kumar et al. |
| 6,613,049 B2 | 9/2003 | Winquist et al. |
| 6,648,583 B1 | 11/2003 | Roy et al. |
| 6,648,891 B2 | 11/2003 | Kim |
| 6,652,524 B1 | 11/2003 | Weiner |
| 6,671,975 B2 | 1/2004 | Hennessey |
| 6,701,174 B1 | 3/2004 | Krause et al. |
| 6,733,502 B2 | 5/2004 | Altarac et al. |
| 6,746,448 B2 | 6/2004 | Weiner et al. |
| 6,769,194 B2 | 8/2004 | Hennessey |
| 6,784,125 B1 | 8/2004 | Yamakawa et al. |
| 6,793,655 B2 | 9/2004 | Orsak |
| 6,860,883 B2 | 3/2005 | Janowski et al. |
| 6,964,663 B2 | 11/2005 | Grant et al. |
| 7,022,122 B2 | 4/2006 | Amrein et al. |
| 7,048,735 B2 | 5/2006 | Ferrante et al. |
| 7,127,660 B2 | 10/2006 | Blaum |
| 7,147,640 B2 | 12/2006 | Huebner et al. |
| 7,197,806 B2 | 4/2007 | Boudreaux et al. |
| 7,226,449 B2 | 6/2007 | Venturini et al. |
| 7,261,713 B2 | 8/2007 | Langmaid et al. |
| 7,276,069 B2 | 10/2007 | Biedermann et al. |
| 7,282,052 B2 | 10/2007 | Mullaney |
| 7,291,148 B2 | 11/2007 | Agee et al. |
| 7,306,601 B2 | 12/2007 | McGrath et al. |
| 7,311,711 B2 | 12/2007 | Cole |
| 7,361,176 B2 | 4/2008 | Cooper et al. |
| 7,377,923 B2 | 5/2008 | Purcell et al. |
| 7,422,593 B2 | 9/2008 | Cresina et al. |

(56) References Cited

U.S. PATENT DOCUMENTS

| | | | |
|---|---|---|---|
| 7,449,023 B2 | 11/2008 | Walulik et al. |
| 7,468,063 B2 | 12/2008 | Walulik et al. |
| 7,479,142 B2 | 1/2009 | Weiner et al. |
| 7,491,008 B2 | 2/2009 | Thomke et al. |
| 7,507,240 B2 | 3/2009 | Olsen |
| 7,527,626 B2 | 5/2009 | Lutz et al. |
| 7,575,575 B2 | 8/2009 | Olsen et al. |
| 7,578,822 B2 | 8/2009 | Rezach et al. |
| RE40,914 E | 9/2009 | Taylor et al. |
| 7,608,074 B2 | 10/2009 | Austin et al. |
| 7,632,271 B2 | 12/2009 | Baumgartner et al. |
| 7,699,848 B2 | 4/2010 | Hoffman et al. |
| 7,708,736 B2 | 5/2010 | Mullaney |
| 7,749,224 B2 | 7/2010 | Cresina et al. |
| 7,763,020 B2 | 7/2010 | Draper |
| 7,803,158 B2 | 9/2010 | Hayden |
| 7,806,843 B2 | 10/2010 | Marin |
| 7,815,586 B2 | 10/2010 | Grant et al. |
| 7,875,030 B2 | 1/2011 | Hoffmann-Clair et al. |
| 7,881,771 B2 | 2/2011 | Koo et al. |
| 7,887,498 B2 | 2/2011 | Marin |
| 7,887,537 B2 | 2/2011 | Ferrante et al. |
| 7,931,650 B2 | 4/2011 | Winquist et al. |
| 7,938,829 B2 | 5/2011 | Mullaney |
| 7,955,333 B2 | 6/2011 | Yeager |
| 7,955,334 B2 | 6/2011 | Steiner et al. |
| 7,985,221 B2 | 7/2011 | Coull et al. |
| 8,029,505 B2 | 10/2011 | Hearn et al. |
| 8,057,474 B2 | 11/2011 | Knuchel et al. |
| 8,114,077 B2 | 2/2012 | Steiner et al. |
| 8,137,347 B2 | 3/2012 | Weiner et al. |
| 8,142,432 B2 | 3/2012 | Matityahu |
| 8,147,490 B2 | 4/2012 | Bauer |
| 8,147,491 B2 | 4/2012 | Lavi |
| 8,157,800 B2 | 4/2012 | Vvedensky et al. |
| 8,172,849 B2 | 5/2012 | Noon et al. |
| 8,182,483 B2 | 5/2012 | Bagnasco et al. |
| 8,187,274 B2 | 5/2012 | Schulze |
| 8,192,434 B2 | 6/2012 | Huebner et al. |
| 8,202,273 B2 | 6/2012 | Karidis |
| 8,241,285 B2 | 8/2012 | Mullaney |
| 8,251,937 B2 | 8/2012 | Marin |
| 8,257,353 B2 | 9/2012 | Wong |
| 8,282,652 B2 | 10/2012 | Mackenzi et al. |
| 8,858,555 B2 | 10/2014 | Crozet et al. |
| 8,906,020 B2 | 12/2014 | Crozet et al. |
| 2001/0025181 A1 | 9/2001 | Freedlan |
| 2001/0049526 A1 | 12/2001 | Venturini et al. |
| 2002/0010465 A1 | 1/2002 | Koo et al. |
| 2002/0013584 A1 | 1/2002 | Termaten |
| 2002/0042613 A1 | 4/2002 | Mata |
| 2002/0165543 A1 | 11/2002 | Winquist et al. |
| 2003/0063949 A1 | 4/2003 | Hohenocker |
| 2003/0069580 A1 | 4/2003 | Langmaid et al. |
| 2003/0106230 A1 | 6/2003 | Hennessey |
| 2003/0109879 A1 | 6/2003 | Orsak |
| 2003/0181911 A1 | 9/2003 | Venturini |
| 2003/0191466 A1 | 10/2003 | Austin et al. |
| 2003/0216734 A1 | 11/2003 | Mingozzi et al. |
| 2003/0225406 A1 | 12/2003 | Weiner et al. |
| 2004/0059331 A1 | 3/2004 | Mullaney |
| 2004/0073211 A1 | 4/2004 | Austin et al. |
| 2004/0073212 A1 | 4/2004 | Kim |
| 2004/0097944 A1 | 5/2004 | Koman et al. |
| 2004/0116926 A1 | 6/2004 | Venturini et al. |
| 2004/0133199 A1 | 7/2004 | Coati et al. |
| 2004/0133200 A1 | 7/2004 | Ruch et al. |
| 2004/0167518 A1 | 8/2004 | Estrada, Jr. |
| 2005/0015087 A1 | 1/2005 | Walulik et al. |
| 2005/0043730 A1 | 2/2005 | Janowski et al. |
| 2005/0059968 A1 | 3/2005 | Grant et al. |
| 2005/0084325 A1 | 4/2005 | O'Brien et al. |
| 2005/0113829 A1 | 5/2005 | Walulik et al. |
| 2005/0119656 A1 | 6/2005 | Ferrante et al. |
| 2005/0149018 A1 | 7/2005 | Cooper et al. |
| 2005/0215997 A1 | 9/2005 | Austin et al. |
| 2005/0234448 A1 | 10/2005 | McCarthy |
| 2005/0248156 A1 | 11/2005 | Hsieh |
| 2005/0251136 A1 | 11/2005 | Noon et al. |
| 2006/0155276 A1 | 7/2006 | Walulik et al. |
| 2006/0184169 A1 | 8/2006 | Stevens |
| 2006/0229605 A1 | 10/2006 | Olsen |
| 2006/0235383 A1 | 10/2006 | Hollawell |
| 2006/0243873 A1 | 11/2006 | Carnevali |
| 2006/0247622 A1 | 11/2006 | Maughan et al. |
| 2006/0247629 A1 | 11/2006 | Maughan et al. |
| 2006/0261221 A1 | 11/2006 | Carnevali |
| 2006/0276786 A1 | 12/2006 | Brinker |
| 2006/0287652 A1 | 12/2006 | Lessig et al. |
| 2007/0038217 A1 | 2/2007 | Brown et al. |
| 2007/0043354 A1 | 2/2007 | Koo et al. |
| 2007/0049930 A1* | 3/2007 | Hearn .................. A61B 17/66 606/56 |
| 2007/0055233 A1 | 3/2007 | Brinker |
| 2007/0055234 A1 | 3/2007 | McGrath et al. |
| 2007/0123857 A1 | 5/2007 | Deffenbaugh et al. |
| 2007/0161983 A1 | 7/2007 | Cresina et al. |
| 2007/0161984 A1 | 7/2007 | Cresina et al. |
| 2007/0162022 A1 | 7/2007 | Zhang et al. |
| 2007/0225704 A1 | 9/2007 | Ziran et al. |
| 2007/0233061 A1 | 10/2007 | Lehmann et al. |
| 2007/0250071 A1 | 10/2007 | Soerensen et al. |
| 2007/0255280 A1 | 11/2007 | Austin et al. |
| 2007/0282338 A1 | 12/2007 | Mullaney |
| 2008/0021451 A1 | 1/2008 | Coull et al. |
| 2008/0228185 A1 | 9/2008 | Vasta et al. |
| 2008/0269741 A1 | 10/2008 | Karidis |
| 2009/0018541 A1 | 1/2009 | Lavi |
| 2009/0036890 A1* | 2/2009 | Karidis .................. A61B 17/62 606/56 |
| 2009/0036891 A1 | 2/2009 | Brown et al. |
| 2009/0105621 A1 | 4/2009 | Boyd et al. |
| 2009/0131935 A1 | 5/2009 | Yeager |
| 2009/0177198 A1* | 7/2009 | Theodoros ............. A61B 17/62 606/56 |
| 2009/0198234 A1 | 8/2009 | Knuchel et al. |
| 2009/0198235 A1 | 8/2009 | Steiner et al. |
| 2009/0264883 A1 | 10/2009 | Steiner et al. |
| 2009/0287212 A1 | 11/2009 | Hirata et al. |
| 2009/0312757 A1 | 12/2009 | Kehres et al. |
| 2010/0087819 A1 | 4/2010 | Mullaney |
| 2010/0145336 A1 | 6/2010 | Draper |
| 2010/0179548 A1 | 7/2010 | Marin |
| 2010/0191239 A1 | 7/2010 | Sakkers et al. |
| 2010/0234844 A1* | 9/2010 | Edelhauser ........... A61B 17/62 606/56 |
| 2010/0249779 A1 | 9/2010 | Hotchkiss et al. |
| 2010/0280516 A1 | 11/2010 | Taylor |
| 2010/0298827 A1 | 11/2010 | Cremer et al. |
| 2010/0305568 A1 | 12/2010 | Ross et al. |
| 2010/0312243 A1 | 12/2010 | Ross et al. |
| 2010/0331840 A1 | 12/2010 | Ross et al. |
| 2011/0060336 A1 | 3/2011 | Pool et al. |
| 2011/0066151 A1 | 3/2011 | Murner et al. |
| 2011/0082458 A1 | 4/2011 | Crozet et al. |
| 2011/0098707 A1 | 4/2011 | Mullaney |
| 2011/0112533 A1 | 5/2011 | Venturini et al. |
| 2011/0118737 A1 | 5/2011 | Vasta et al. |
| 2011/0118738 A1 | 5/2011 | Vasta et al. |
| 2011/0172663 A1 | 7/2011 | Mullaney |
| 2011/0172664 A1 | 7/2011 | Bagnasco et al. |
| 2011/0245830 A1 | 10/2011 | Zgonis et al. |
| 2011/0313418 A1 | 12/2011 | Nikonovas |
| 2011/0313419 A1 | 12/2011 | Mullaney |
| 2012/0004659 A1 | 1/2012 | Miller et al. |
| 2012/0041439 A1 | 2/2012 | Singh et al. |
| 2012/0078251 A1 | 3/2012 | Benenati et al. |
| 2012/0089142 A1 | 4/2012 | Mullaney et al. |
| 2012/0095462 A1 | 4/2012 | Miller |

(56) References Cited

U.S. PATENT DOCUMENTS

| | | |
|---|---|---|
| 2012/0136355 A1 | 5/2012 | Wolfson |
| 2012/0143190 A1 | 6/2012 | Wolfson |
| 2013/0253512 A1 | 9/2013 | Crozet et al. |
| 2014/0378972 A1 | 12/2014 | Crozet et al. |

FOREIGN PATENT DOCUMENTS

| | | |
|---|---|---|
| DE | 202006006734 U1 | 6/2006 |
| EP | 0377744 A1 | 7/1990 |
| EP | 611007 A1 | 8/1994 |
| EP | 1016381 A1 | 7/2000 |
| EP | 1136041 A2 | 9/2001 |
| EP | 2417923 A1 | 2/2012 |
| EP | 2417924 A1 | 2/2012 |
| FR | 2439002 A1 | 5/1980 |
| FR | 2576774 A1 | 8/1986 |
| FR | 2756025 A1 | 5/1998 |
| IT | 1259768 B | 3/1996 |
| WO | 92/14426 | 9/1992 |
| WO | 9418898 | 9/1994 |
| WO | 97/30650 | 8/1997 |
| WO | 97/30651 | 8/1997 |
| WO | 01/15611 A1 | 3/2001 |
| WO | 01/22892 A1 | 4/2001 |
| WO | 01/78613 | 10/2001 |
| WO | 03/086213 | 10/2003 |
| WO | 2006116307 | 11/2006 |
| WO | 2007075114 | 7/2007 |
| WO | 2007111576 A2 | 10/2007 |
| WO | 2009100459 A1 | 8/2009 |
| WO | 2010104567 A1 | 9/2010 |
| WO | 2012102685 A1 | 8/2012 |

OTHER PUBLICATIONS

S.V. Sreenivasan et al., "Closed-Form Direct Displacement Analysis of a 6-6 Stewart Platform," Mech. Mach. Theory, vol. 29, No. 6, pp. 855-864, 1994.
Hwang et al., Asian Journal of Control, vol. 6, No. 1, pp. 136-144, Mar. 2004.
European Search Report, EP 08 15 0960 dated Jul. 30, 2008.
Smith&Nephew, Taylor Spatial Frame, website printout, Aug. 12, 2009.
Alizade et al., Mech. Mach. Theory, vol. 29, No. 1, pp. 115-124, 1994, Great Britain, © 1993.
International Search Report and Written Opinion, PCT/US2010/000712, dated Jun. 28, 2010.
European Search Report, EP 08 15 4761 dated Aug. 21, 2008.
European Search Report, EP 08 15 4754 dated Jul. 4, 2008.
European Search Report, EP 08 15 0944 dated Aug. 18, 2008.
Biomet® Vision™ Footring™ System: Surgical Technique, 39 pages, (2008).
European Search Report, EP 10 172 523 dated Mar. 25, 2011.
European Search Report, EP 11176512, dated Sep. 19, 2011.
European Search Report, EP 11176566, dated Sep. 20, 2011.
U.S. Appl. No. 13/788,466, filed Mar. 7, 2013 (not yet published).
Nanua et al., IEEE Transactions on Robotics and Automation, vol. 6, No. 4, pp. 438-444, Aug. 1990.
Partial European Search Report for Application No. EP13180720 dated Dec. 3, 2013.
Extended European Search Report for Application No. EP13180720 dated Apr. 15, 2014.
European Search Report for Application No. EP15167691 dated Sep. 17, 2015.
Extended European Search Report EP16170790, dated Dec. 19, 2016, 5 pages.

* cited by examiner

SECTION A-A

SECTION B-B

SECTION C-C

SECTION D-D

SECTION E-E

SECTION F-F

SECTION G-G

SECTION H-H

BONE TRANSPORT EXTERNAL FIXATION FRAME

CROSS-REFERENCE TO RELATED APPLICATIONS

The present application is a continuation of U.S. patent application Ser. No. 13/592,832, filed Aug. 23, 2012, the disclosure of which is hereby incorporated by reference herein.

FIELD OF THE INVENTION

The present invention relates to systems and methods for manipulating the orientation of a plurality of bone fragments with respect to one another, and in particular it relates to external fixation devices in which rings thereof may be manipulated with respect to one another via bone transport assemblies.

BACKGROUND OF THE INVENTION

External fixation frames may be used to correct skeletal deformities using the distraction osteogenesis process. The Ilizarov external fixation devices, for example, are widely used for this purpose. The Ilizarov-type devices may be used to translate bone segments by manipulating rings connected to each bone segment.

External fixation devices generally utilize a plurality of threaded rods fixated to through-holes in the rings to build the frame. In order to build a desired frame, these rods generally have to have different lengths. A problem that may arise out of this is that such external fixation frames generally do not allow significant manipulation of what may be referred to as a transport ring without disassembling and then reassembling the frame or adding new devices. These systems generally require removal of the entire frame in order to perform reconstruction.

Once the frame is installed, the patient or surgeon generally moves the rings or percutaneous fixation components manually or mechanically by adjusting a series of adjustment mechanism, such as nuts, for example. A traditional method of adjusting the frame height generally requires the surgeon to loosen an individual nut gradually while tightening another other nut in order to secure the frame. These position adjustments must be done where the nuts are secured, making it very difficult for the patient to make the required daily adjustments with consideration of stable fixation in mind. Other devices use different techniques to adjust the effective length of the rods, but all must be adjusted somewhere between the ends, offering limited access for the patient.

As adjustments made to external fixation devices are often a daily task for the patient, easy access to frame adjustment mechanisms would be beneficial for the patient.

BRIEF SUMMARY OF THE INVENTION

A first aspect of the present invention is a bone transport frame including first and second rings, a plurality of elongate struts, and a plurality of ring transport assemblies. The first and second rings each have upper and lower ring surfaces and a central axis that is perpendicular to the upper and lower ring surfaces. The plurality of elongate struts each having a central axis and are coupled to the first and second rings, the plurality of elongate struts each include a first adjustable member. The plurality of ring transport assemblies are adapted to rotatably couple the second ring to the plurality of elongate struts, the plurality of ring transport assemblies each include a second adjustable member. Preferably, rotation of the first adjustable member transports the second ring in either a proximal or distal direction with respect to the first ring, and rotation of the second adjustable member translates the central axis of the second ring either toward or away from each central axis of the plurality of elongate struts.

In accordance with one embodiment of this first aspect of the present invention, the bone transport frame includes a third ring having upper and lower ring surfaces and having a central axis that is perpendicular to the upper and lower ring surfaces. The third ring is also coupled to the plurality of elongate struts and is located distally to the second ring, the second ring being located distally to the first ring.

In accordance with another embodiment of this first aspect, the first, second and third rings each include a plurality of through-holes that extend through the upper and lower ring surfaces.

In accordance with yet another embodiment of this first aspect, the bone transport frame further includes a plurality of pin retention members and bone pins adapted to couple the first, second, and third rings to a first, second and third bone fragments, respectively. The plurality of pin retention members are operatively coupled to the plurality of through-holes of the first, second and third rings.

In accordance with still yet another embodiment of this first aspect, the bone transport frame further includes a plurality of wire retention members and bone wires adapted to couple the first, second and third rings to the first, second and third bone fragments, respectively. The plurality of wire retention members are operatively coupled to the plurality of through-holes of the first, second, and third rings.

In accordance with still yet another embodiment of this first aspect, the bone transport frame further includes a plurality of flange extension members adapted to couple the first ring to the plurality of elongate struts, wherein each of the plurality of flange extension members include a first through-hole adapted to receive a first coupling member for coupling a first end of the plurality of flange extension members to the first ring and a second through hole adapted to receive a proximal end portion of the plurality of elongate struts. Each of the plurality of flange extension members further comprises a third through-hole adapted to receive a second coupling member for rigidly coupling the first end of the plurality of flange extension members to the first ring.

In accordance with still yet another embodiment of this first aspect, the first adjustable member of each of the plurality of elongate struts is located at the proximal end portion of the plurality of elongate struts. The first adjustable member of each of the plurality of elongate struts is adapted to make incremental adjustments, each incremental adjustment corresponding to a clinically optimal adjustment length. The first adjustable member of each of the plurality of elongate struts is adapted to record each incremental adjustment.

In accordance with still yet another embodiment of this first aspect, the plurality of elongate struts further includes a threaded shaft and a position adjustment member coupled to each of the plurality of ring transport assemblies, each position adjustment member adapted to transport along a length of the threaded shaft in the proximal and distal directions. Each position adjustment member has a semi-locked position such that the location of each position adjustment member on the threaded shaft is constant when the threaded shaft is not being rotated in either clockwise or counterclockwise directions about the central axis of the plurality of elongate struts and has an unlocked position such that the location of each position adjustment member can transport in either the proximal or distal directions without the threaded shaft being rotated in either the clockwise or counterclockwise directions about the central axis of the plurality of elongate struts.

In accordance with still yet another embodiment of this first aspect, each of the plurality of ring transport assemblies further comprises a third adjustment member and wherein releasing the third adjustment member allows the second ring to move such that the central axis of the second ring is oblique to the central axis of each of the plurality of elongate struts.

In accordance with still yet another embodiment of this first aspect, the second adjustment member is coupled to the third adjustment member, the second adjustment member being adapted to incrementally translate the central axis of the second ring either toward or away from each central axis of the plurality of elongate struts.

A second aspect of the present invention is a method for transporting a second bone segment with respect to a first bone segment utilizing a bone transport frame including a first ring, a second ring, a plurality of ring transport assemblies, a plurality of first and second adjustment mechanisms, and a plurality of elongate struts. The method includes coupling the first bone segment to the first ring; coupling the second bone segment to the second ring; actuating the first adjustment mechanism to transport the second ring in either a proximal or distal direction along a central axis of at least one of the plurality of elongate struts; and actuating the second adjustable member to translate the second ring either toward or away from each of the plurality of elongate struts.

In accordance with one embodiment of this second aspect, the step of actuating the first adjustment mechanism comprises incrementally rotating the first adjustment mechanism such that the second ring transports a fixed length along the central axis of at least one of the plurality of elongate struts, each incremental rotation of the first adjustment mechanism corresponding to a first fixed length. The step of actuating the second adjustable member comprises incrementally rotating the second adjustment mechanism such that the second ring translates either toward or away from each of the plurality of elongate struts, each incremental rotation of the second adjustment mechanism corresponding to a second fixed length.

In accordance with another embodiment of this second aspect, the step of coupling the first bone segment to the first ring comprises coupling a first end of a bone pin to the first bone segment and coupling a second end of the bone pin to a pin retention member, the pin retention member being coupled to the first ring. The step of coupling the first bone segment to the first ring comprises coupling a first end of a bone wire to the first bone segment and coupling a second end of the bone wire to a wire retention member, the wire retention member being coupled to the first ring.

In accordance with yet another embodiment of this second aspect, the method further includes transporting a position adjustment member along a length of one of the plurality of elongate strut members in the proximal or distal direction, the position adjustment member being in an unlocked state and being coupled to one of the plurality of bone transport assemblies; and locking the position adjustment member into a semi-locked state such that the position adjustment member engages a thread of the elongate strut member and such that the position adjustment member is unable to transport along a length of the elongate strut member in the proximal or distal direction independently of rotation of the thread.

A third aspect of the present invention is a bone transport frame including first and second rings, a plurality of elongate struts, and a plurality of ring transport assemblies. The first and second rings each have upper and lower ring surfaces and a central axis that is perpendicular to the upper and lower ring surfaces. The plurality of elongate struts each having a central axis and are coupled to the first and second rings, the plurality of elongate struts each include a first adjustable member. Rotation of the first adjustable member transports the second ring in either a proximal or distal direction along the central axis of at least one of the plurality of elongate struts. The plurality of ring transport assemblies are adapted to rotatably couple the second ring to the plurality of elongate struts, wherein at least one of the plurality of ring transport assemblies comprises a flange and a ball joint, a first end of the flange being coupled to the second ring and a second end of the flange being coupled to one of the plurality of elongate struts, the ball joint enabling the second ring to rotate with respect to the plurality of elongate struts such that the central axis of the second ring is oblique to the central axis of each of the plurality of elongate struts.

BRIEF DESCRIPTION OF THE DRAWINGS

Other aspects, aims and advantages of the present invention will become more apparent on reading the following detailed description of preferred embodiments thereof, given by way of example, and with reference being made to the attached drawings, in which.

DETAILED DESCRIPTION

Where possible, identical or similar elements or parts are designated by the same reference labels.

The term "proximal" and "distal" used throughout the present description correspond, respectively, to that end of the bone transport frame nearest the patient's heart and the end of the bone transport frame farthest from the patient's heart.

Figure 1:
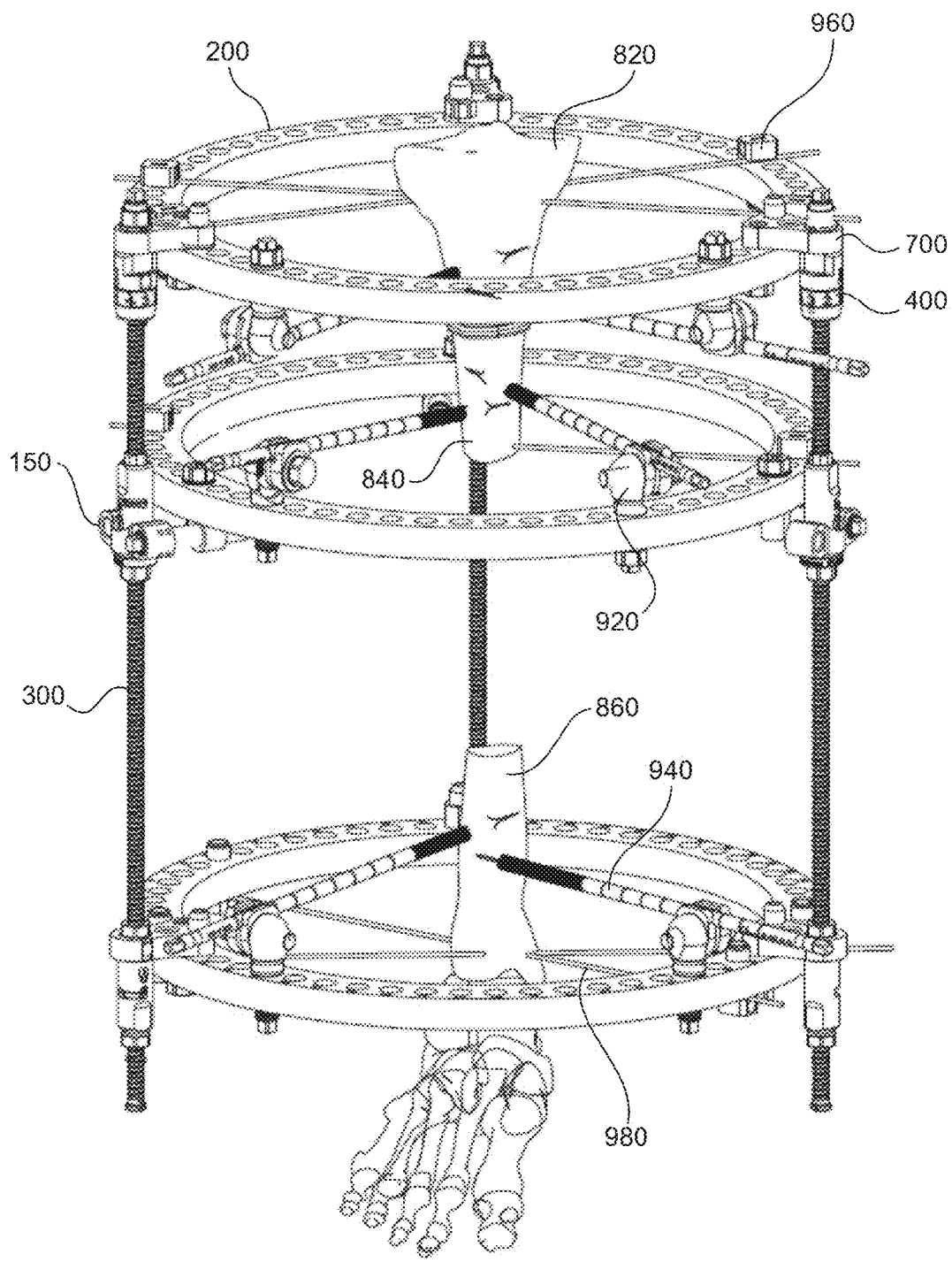
FIG. 1 is a perspective view of one embodiment of a bone transport frame in accordance with the present invention.
Figure 2:
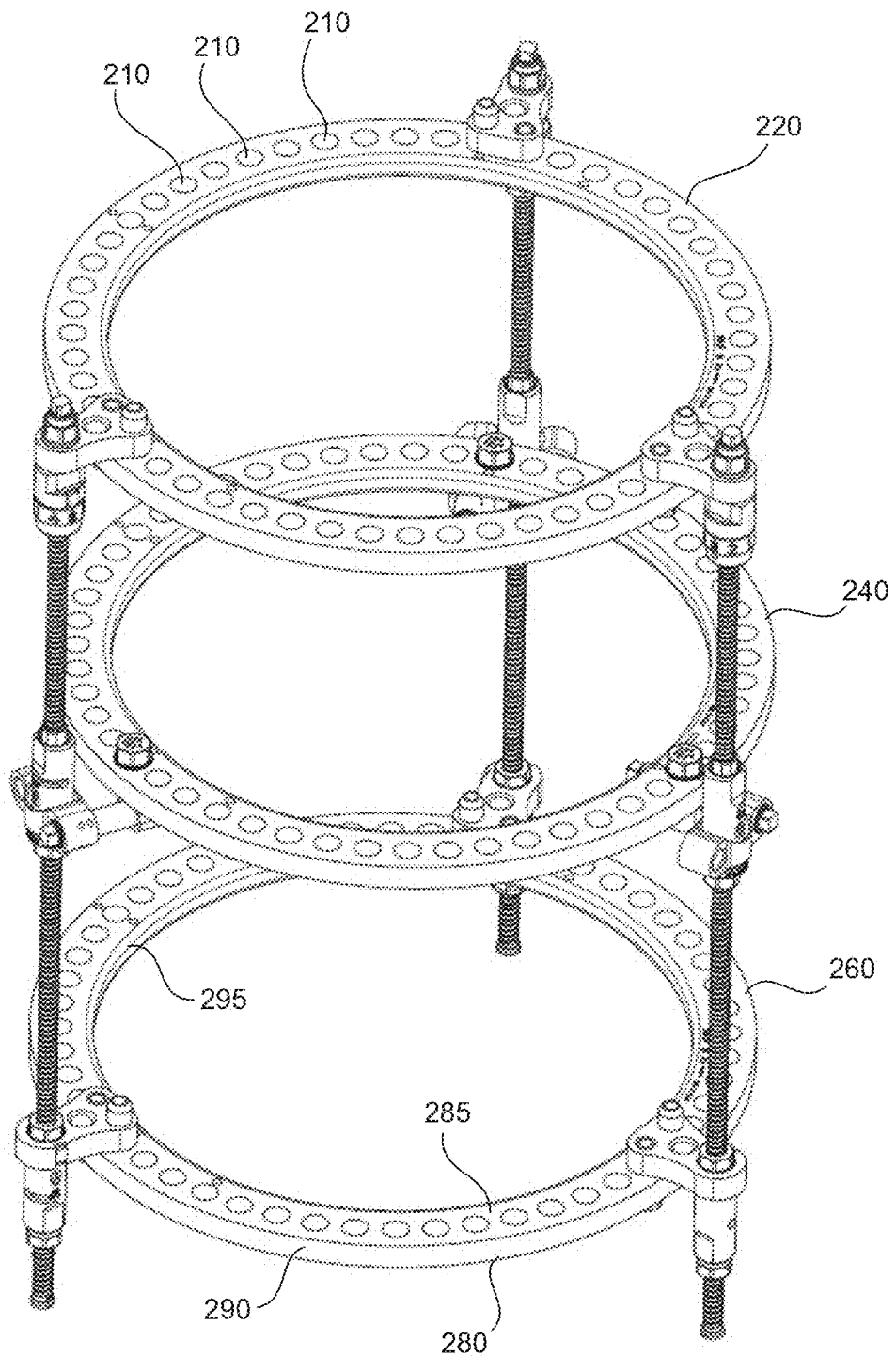
FIG. 2 is an isometric view of the bone transport frame of FIG. 1.
Figure 3:
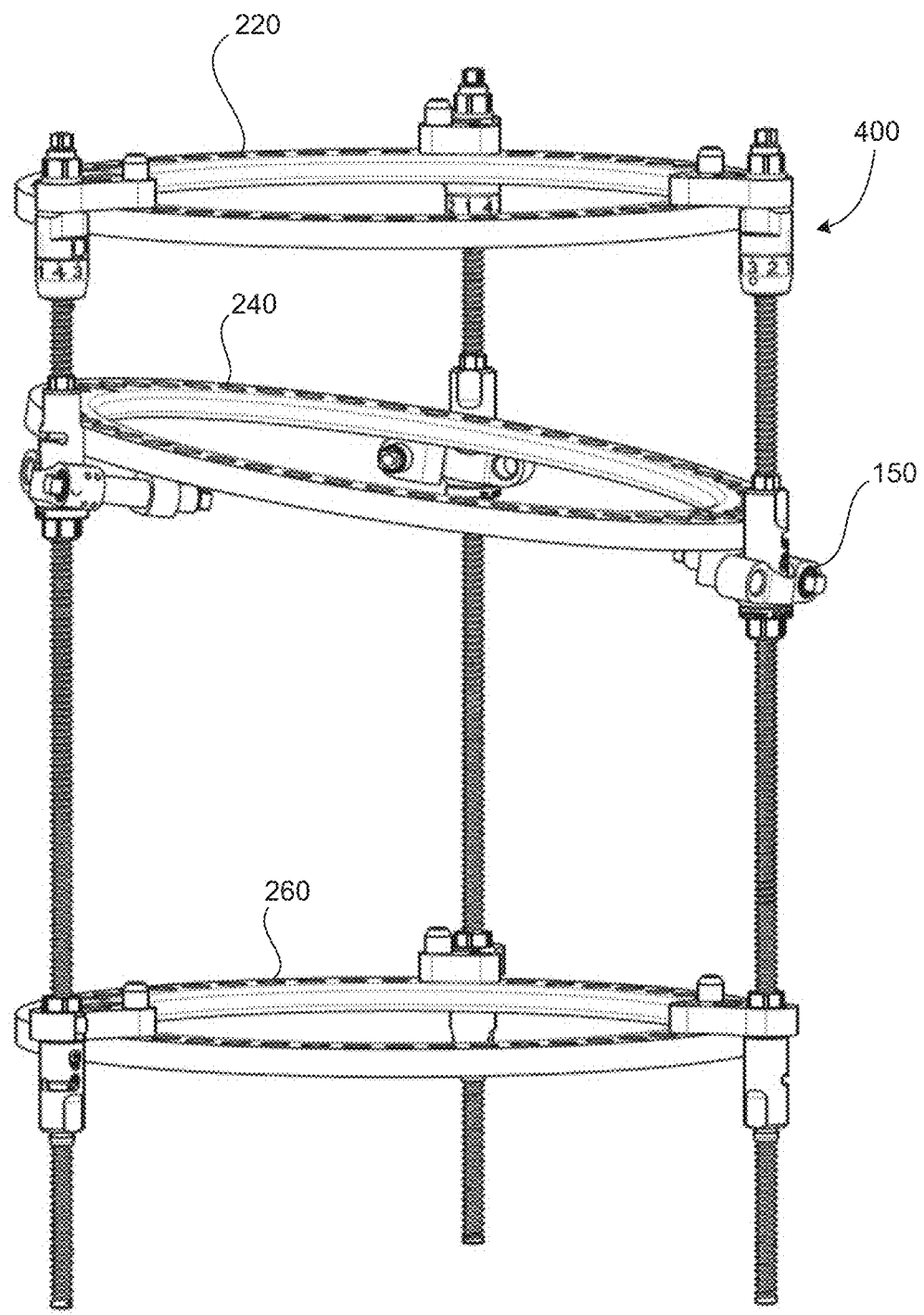
FIG. 3 is an exemplary view showing ring manipulation of the bone transport frame of FIG. 1 in accordance with the present invention.
Figure 4:
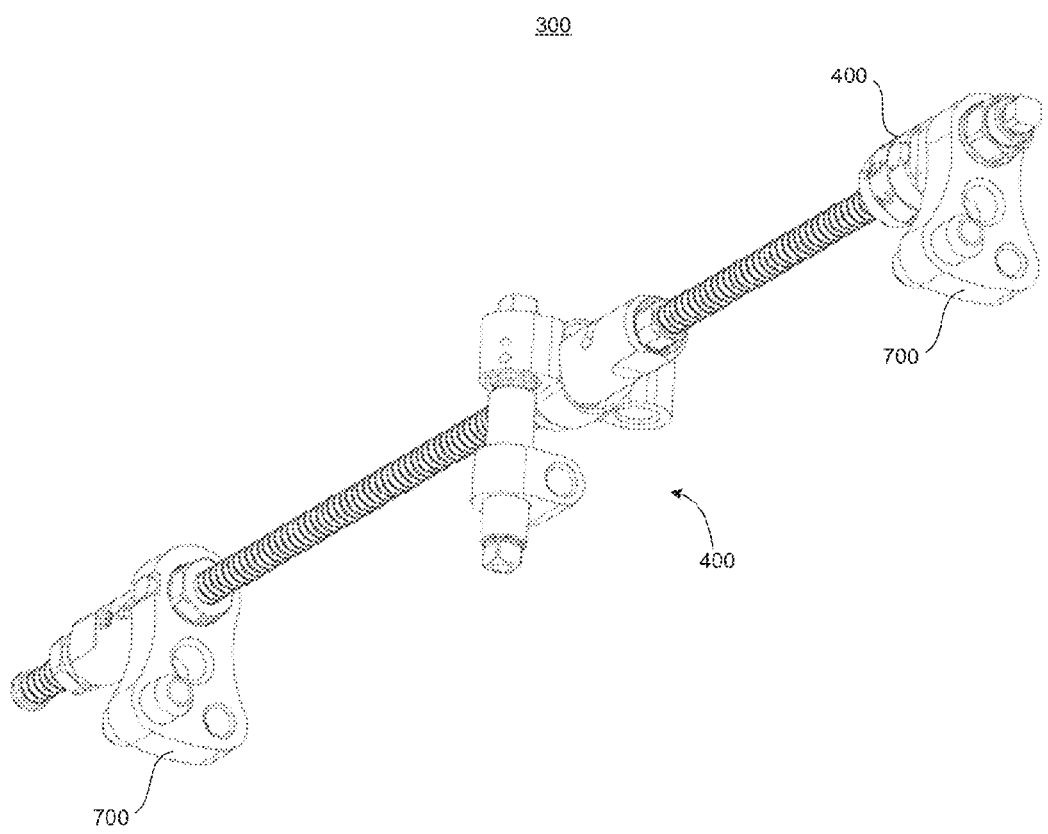
FIG. 4 is a perspective view of a strut assembly of the bone transport frame of FIG. 1.

Referring to FIGS. 1-3, a first embodiment of a bone transport frame 100 is shown. The bone transport frame 100 generally comprises a plurality of bone transport assemblies 150, a plurality of bone transport rings 200, a plurality of strut assemblies 300, a plurality of top click mechanisms 400, and a plurality of devices that interact with different segments or portions of a bone.

Each of the bone transport rings 200 has a lower ring surface 280 and an upper ring surface 285 as well as an outer ring surface 290 and an inner ring surface 295. Upper 285, lower 280, inner 295, and outer 290 ring surfaces are substantially flat such that each ring has a vertical cross section that is substantially rectangular. In other embodiments, ring surfaces 280, 285, 290 and 295 need not be flat, but rather can take on various shapes to accommodate other devices such as clamps, for example.

Along the circumference of each of the bone transport rings 200 resides a plurality of through-holes 210 that extend through both the upper 285 and lower 280 ring surfaces. The through-holes 210 facilitate mechanical connections between the strut assemblies 300 and numerous other devices the surgeon may deem necessary during use of bone transport frame 100.

Such devices, for example, include bone-pin retaining devices 920 and bone-wire retaining devices 960. Due to the substantially flat contours of the ring surfaces and the plurality of through-holes 210, a user is provided significant flexibility in appropriately placing the bone-pin retaining devices 920 and bone-wire retaining devices 960 at desired locations. Thus, a user can couple any of these devices at numerous locations around the circumference of each of the bone transport rings 200 as well as coupling the devices at the upper 285 or lower 280 ring surfaces of the bone transport rings 200. Devices that can be used to facilitate interaction between the bone transport frame 100 and portions of a bone include, for example, a series of bone-wires 980 and bone-pins 940.

As shown in FIGS. 1 and 2, bone transport frame 100 includes a proximal ring 220, a medial ring 240, and a distal ring 260 wherein the proximal ring 220 is affixed to a first bone segment 820, the medial ring 240 is affixed to a second bone segment 840, and the distal ring 260 is affixed to a third bone segment 860. The first bone segment 820 and second bone segment 840 are typically separated by an osteotomy created in the bone to allow for osteogenesis as the second bone segment is incrementally transported toward the third bone segment 840. The second bone segment 820 and third bone segment 860 are typically separated by a deformity, such as a fracture or the like.

Strut assemblies 300 act to stabilize the bone segments and to provide for transportation thereof. FIGS. 1-3 show bone transport frame 100 including three strut assemblies 300, but in other embodiments more than three strut assemblies 300 may be utilized, such as four, five, six or more strut assemblies 300, for example.

Figure 5:
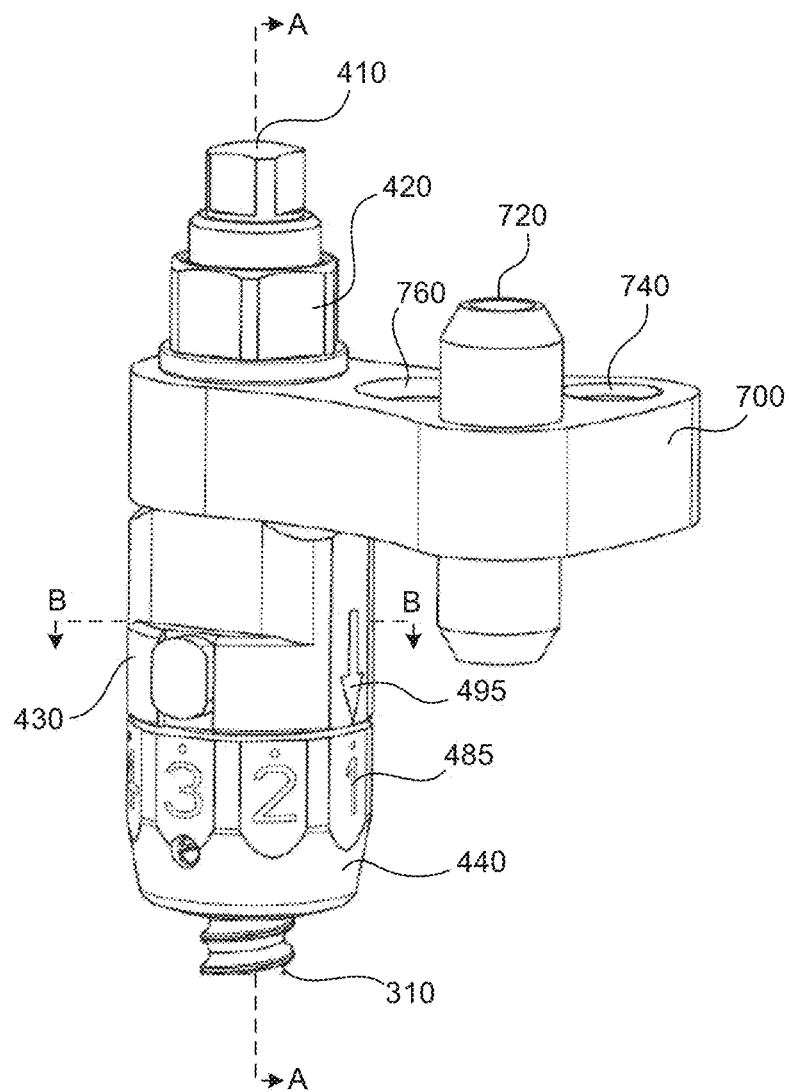
FIG. 5 is a perspective view of a top click mechanism and flange of the bone transport frame of FIG. 1.
Figure 6:
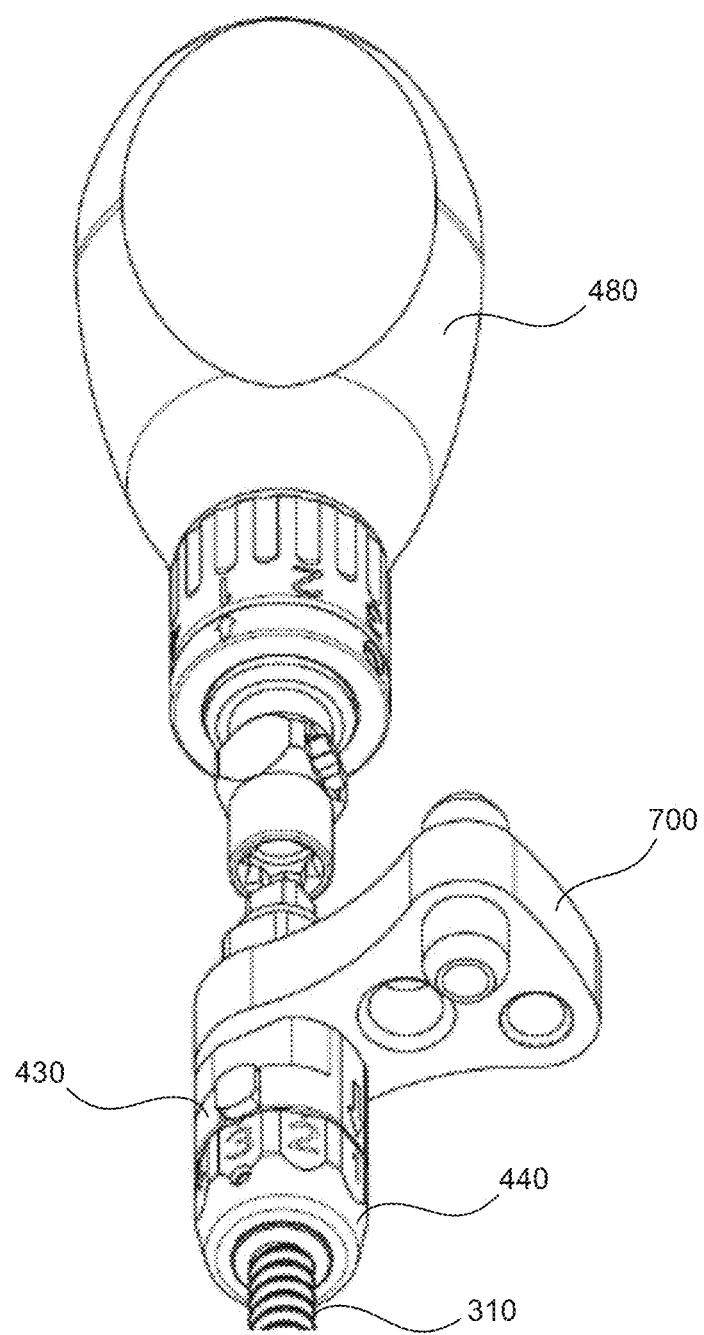
FIG. 6 is a perspective view of the top click mechanism of FIG. 5 and a top click mechanism screw driver.
Figure 7:
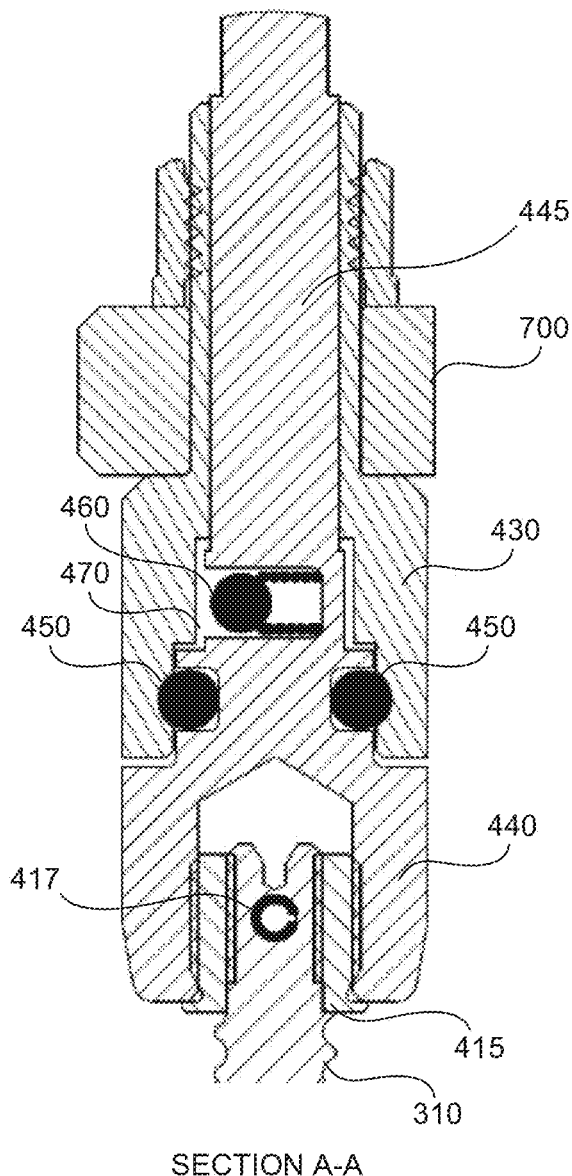
FIG. 7 is a vertical cross sectional view of the top click mechanism of FIG. 5 at A-A.

Referring to FIGS. 4-8, the proximal end of each strut assembly 300 includes a top click mechanism 400. The top-click mechanism 400 includes a square head 410, a clamping nut 420, a clicking body 430, a driver body 440, a spring and ball system 460, and a series of retaining balls 450. The square head 410 provides an interface to mate with a screw driver 480 as shown in FIG. 6. The clamping nut 420 clamps a flange 700 to the top-click mechanism 400.

The driver body 440 is rigidly coupled to the strut 310 via a coupling member 415 and pin 417 so that rotation of the driver body 440 causes the strut 310 to rotate in unison with the driver body 440. Further, the driver body 440 has an elongated portion 445 which terminates at the proximal end thereof as at square head 410.

A clicking body 430 fits over the elongated portion 445 of the driver body 440 like a sleeve, for example. The clicking body 430 is axially retained by a series of retaining balls 450 that allow the clicking body 430 to rotate with respect to the driver body 440 without translating with respect to the driver body.

Figure 8:
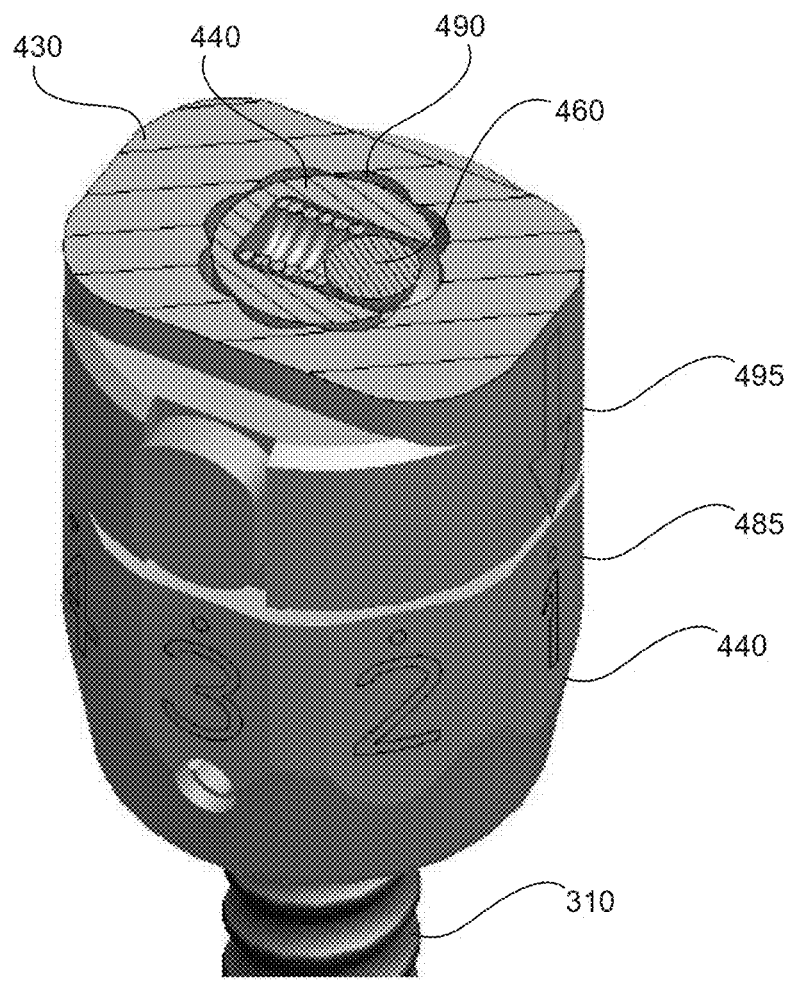
FIG. 8 is a horizontal cross sectional view of the top click mechanism of FIG. 5 at B-B.

A cylindrical notch 470 is formed within the elongated portion of the driver body 440. Within this cylindrical notch 470 resides a detent means in the form of a spring and ball system 460, for example, which communicates with a series of recesses 490 on the internal portion of the clicking body 430 as shown in FIG. 8. The recesses or profile cuts 490 are created so that a portion of the ball of the spring and ball system 460 sits in and partially conforms to each of the profile cuts 490. Further, the profile cuts 490 are such that as the driver body 440 is rotated, the ball of the ball and spring system 460 is capable of translating to an adjacent profile cut 490 creating a clicking sound and feel.

Each profile cut 490 should be spaced and each strut 310 should be threaded so that each click corresponds with the strut 310 rotating a sufficient amount to cause the medial ring 240 to axially translate along the strut 310 a clinically optimal length. In one embodiment, the clinically optimal length is approximately 0.25 mm. At a rate of four "clicks" per day, the rate of osteogenesis between the first bone segment 820 and second bone segment 840 will be approximately 1 mm per day. However, a single "click" can correspond to different distances lengths, depending on the specific needs for a particular situation.

The ball and spring system 460 additionally functions to constrain the driver body 440 and strut 310 from the rotation provided by the retaining balls 450. Thus, the driver body 440 and strut 310 cannot rotate until a screw driver 480 applies the proper torque to the square nut 410 to overcome the force of the spring and ball system 460 and translate the ball to the adjacent profile cut 490.

An arrow 495 as shown in FIG. 8 that points distally is etched on the outer surface of the clicking body 430 and is lined up with a corresponding number 485 etched on the outer surface of the driver body 440. The numbers 485 are spaced such that each click corresponds to a rotation of the arrow 495 from a first number 485 to an adjacent number 485. Preferably, the numbers 485 are placed on the flat surfaces of an octagon and numbered 1-4 and 4-1. This numbering is done so that the patient can keep track of the preferred four adjustments per day, for example. The clicking mechanism as disclosed in U.S. Patent Application Publication No. 2012/0041439 is hereby incorporated by reference herein in its entirety.

As best seen in FIG. 5, a flange 700 extends from the outer surface of a portion of the clicking body 430 and is clamped against the clicking body 430 by a clamping nut 420. When the flange 700 is coupled to a transport ring 200, clamping the flange 700 will not only secure the flange to the clicking body 430 but also prohibits the clicking body 430 from rotating with the driver body 440 and strut 310.

Figure 9:
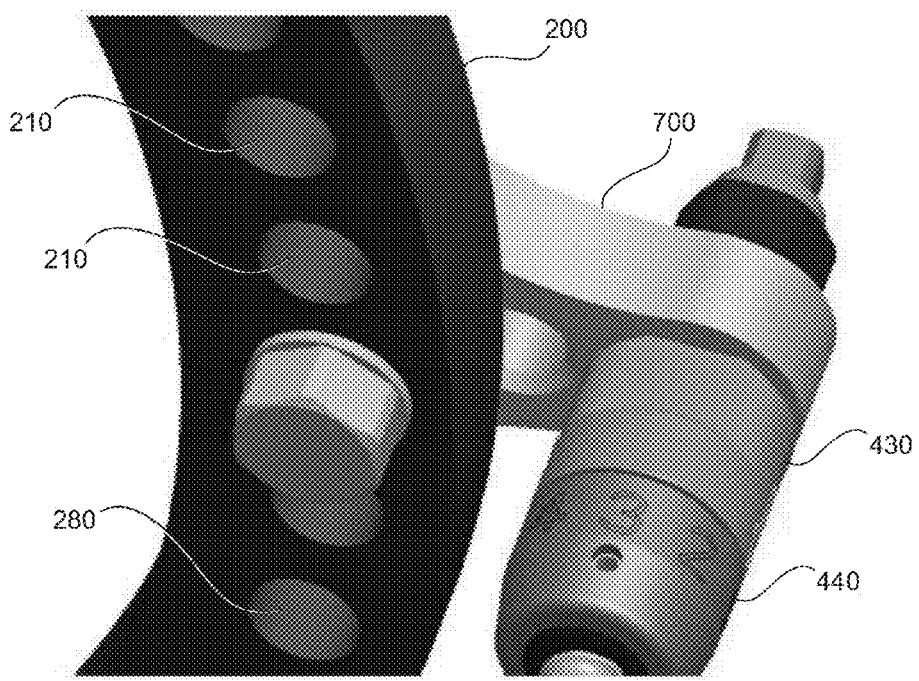
FIG. 9 is a perspective view illustrating a bolted connection between a ring of the bone transport frame of FIG. 1 and the top click mechanism and flange of FIG. 5.

The flange 700 includes anterior through-holes 740 and a medial through-hole 760 in a triangular pattern. The anterior through-holes 740 are the primary junctions for coupling the flange 700 to the bone transport rings 200. A single retaining pin 720 can be used to couple the flange 700 to the through-holes 210 of the transport rings 200. Alternately, both anterior through-holes 740 can be used, each in conjunction with a retaining pin 720, to provide an anti-torque function that prevents rotation of the flange 700 with respect to the transport ring 200. Other connection mechanisms besides retaining pints 720 can be used. For example, a user may choose to use a bolt and nut system in lieu of the retaining pin to secure the flange to the transport ring as seen in FIGS. 9-10.

Figure 10:
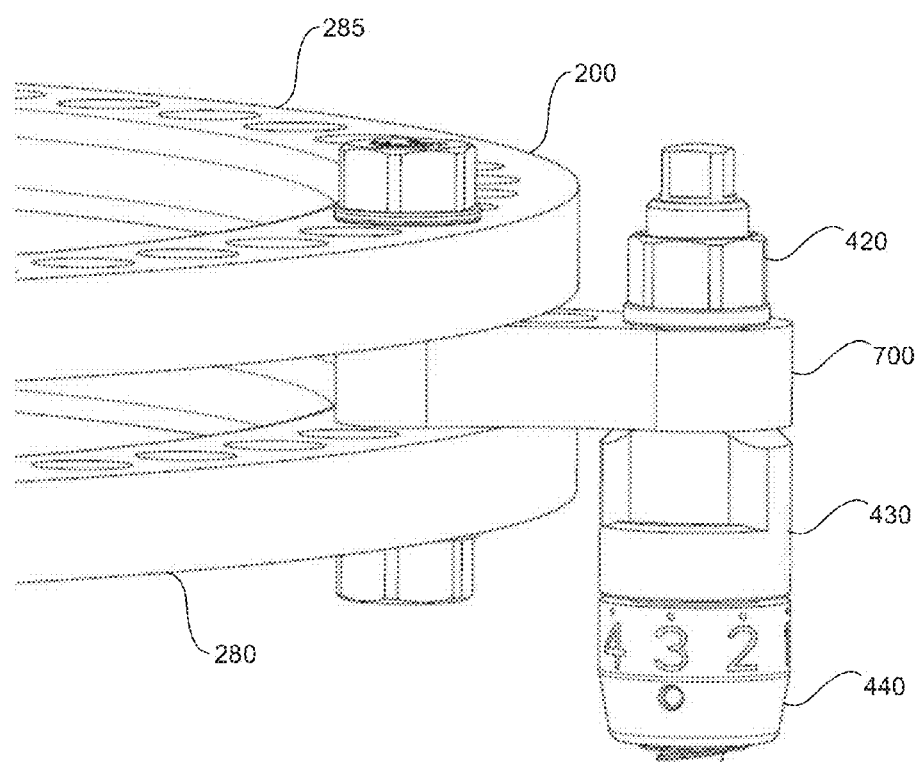
FIG. 10 is a perspective view illustrating the capability of the flange of FIG. 5 to be mechanically connected to either the top or bottom of a ring of the bone transport frame of FIG. 1.
Figure 11:
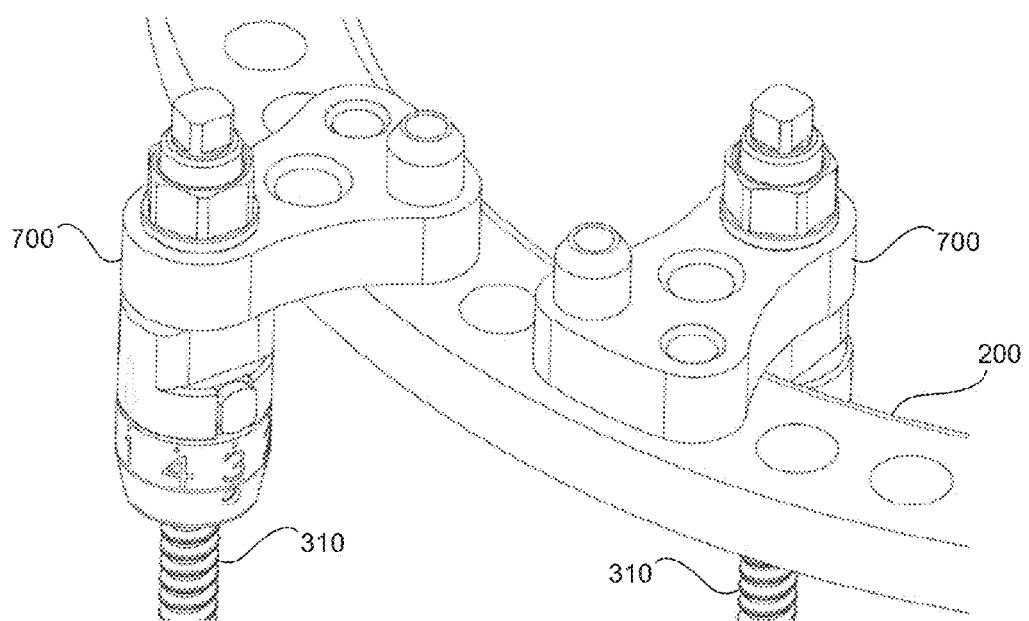
FIG. 11 is a perspective view illustrating the capability of the strut assembly of FIG. 4 to be connected to either the inside or outside of a ring of the bone transport frame of FIG. 1.
Figure 12:
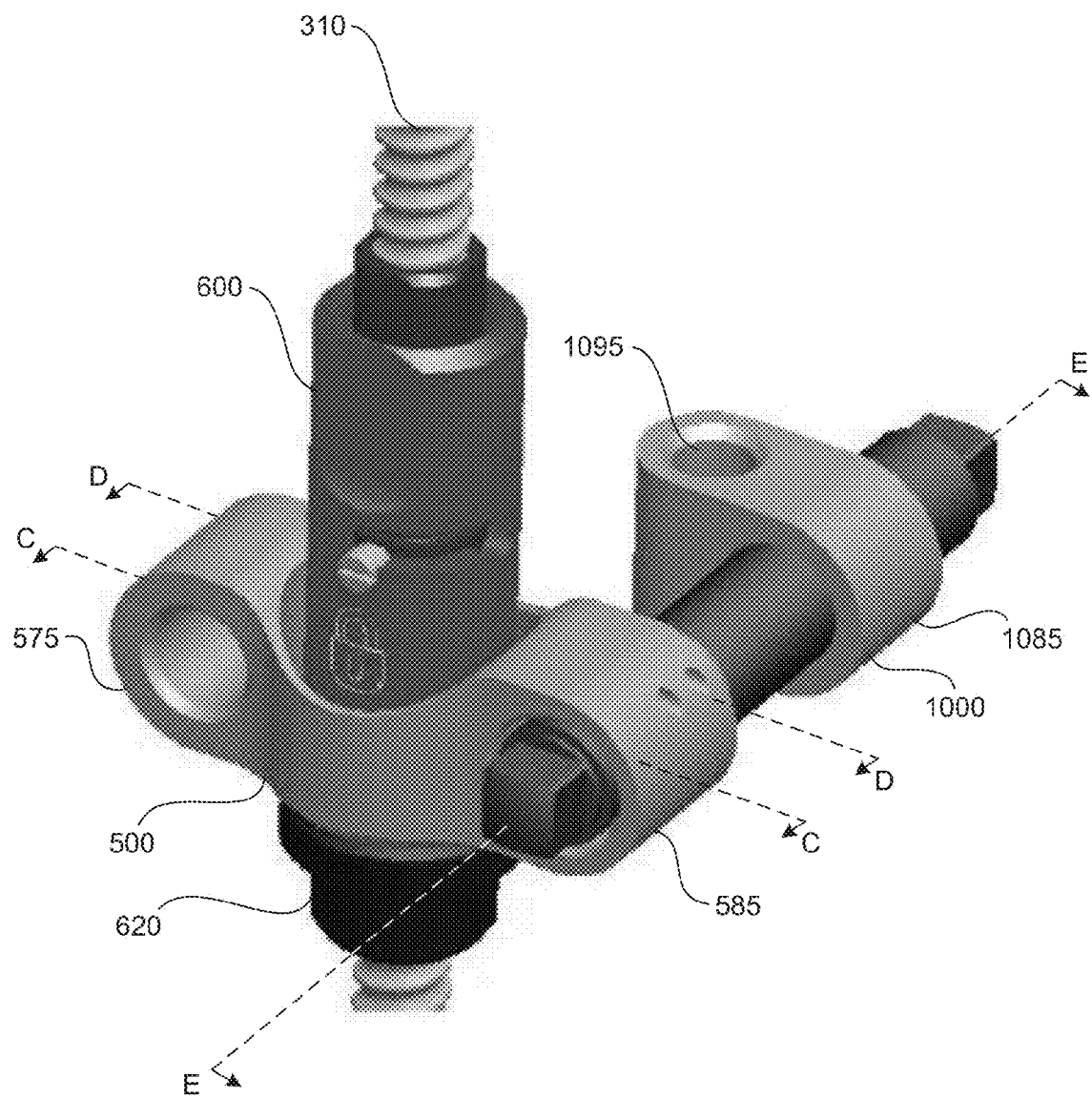
FIG. 12 is a perspective view of one embodiment of a bone transport assembly of the bone transport frame of FIG. 1 in accordance with the present invention.
Figure 13:
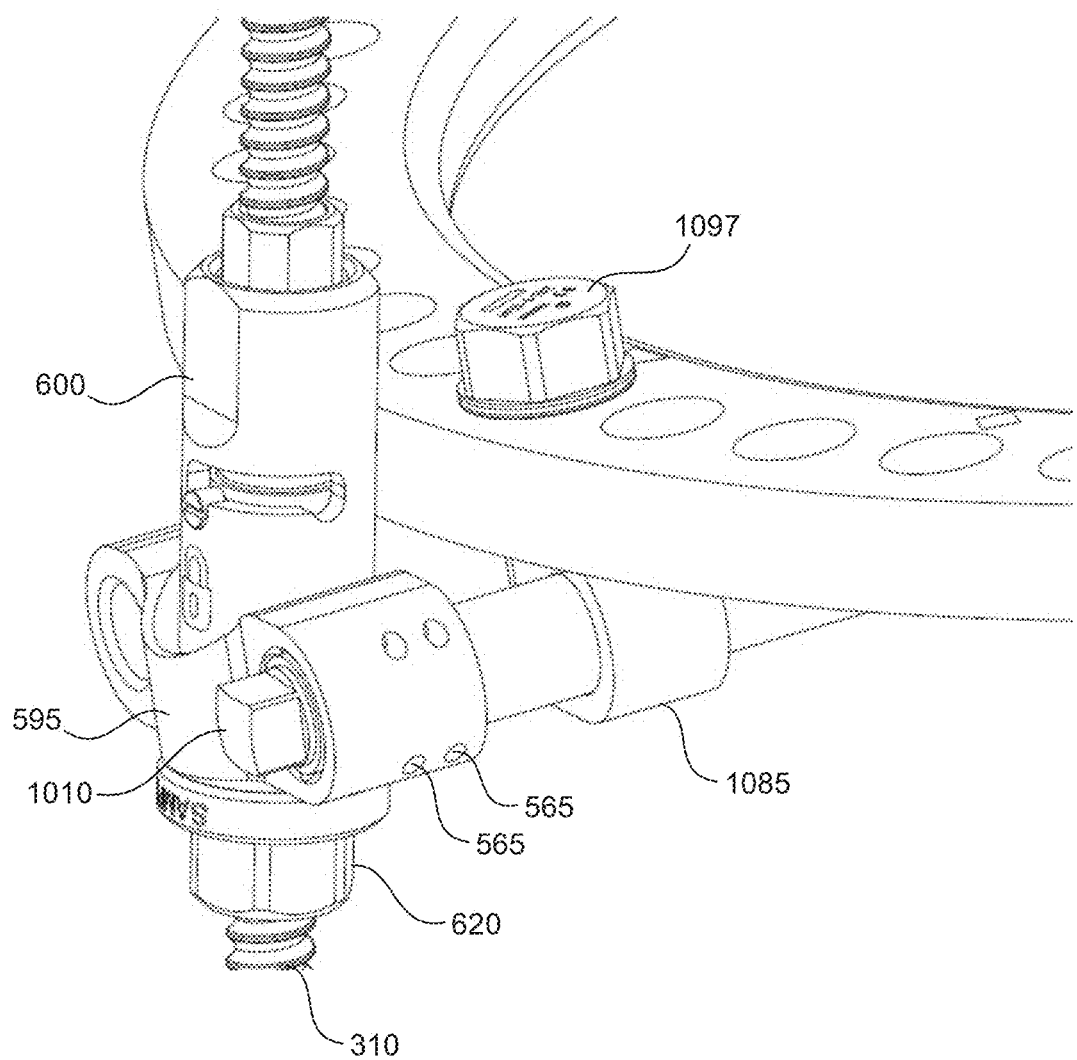
FIG. 13 is a perspective view illustrating the connection between a bone transport assembly and a ring of the bone transport frame of FIG. 1.
Figure 14:
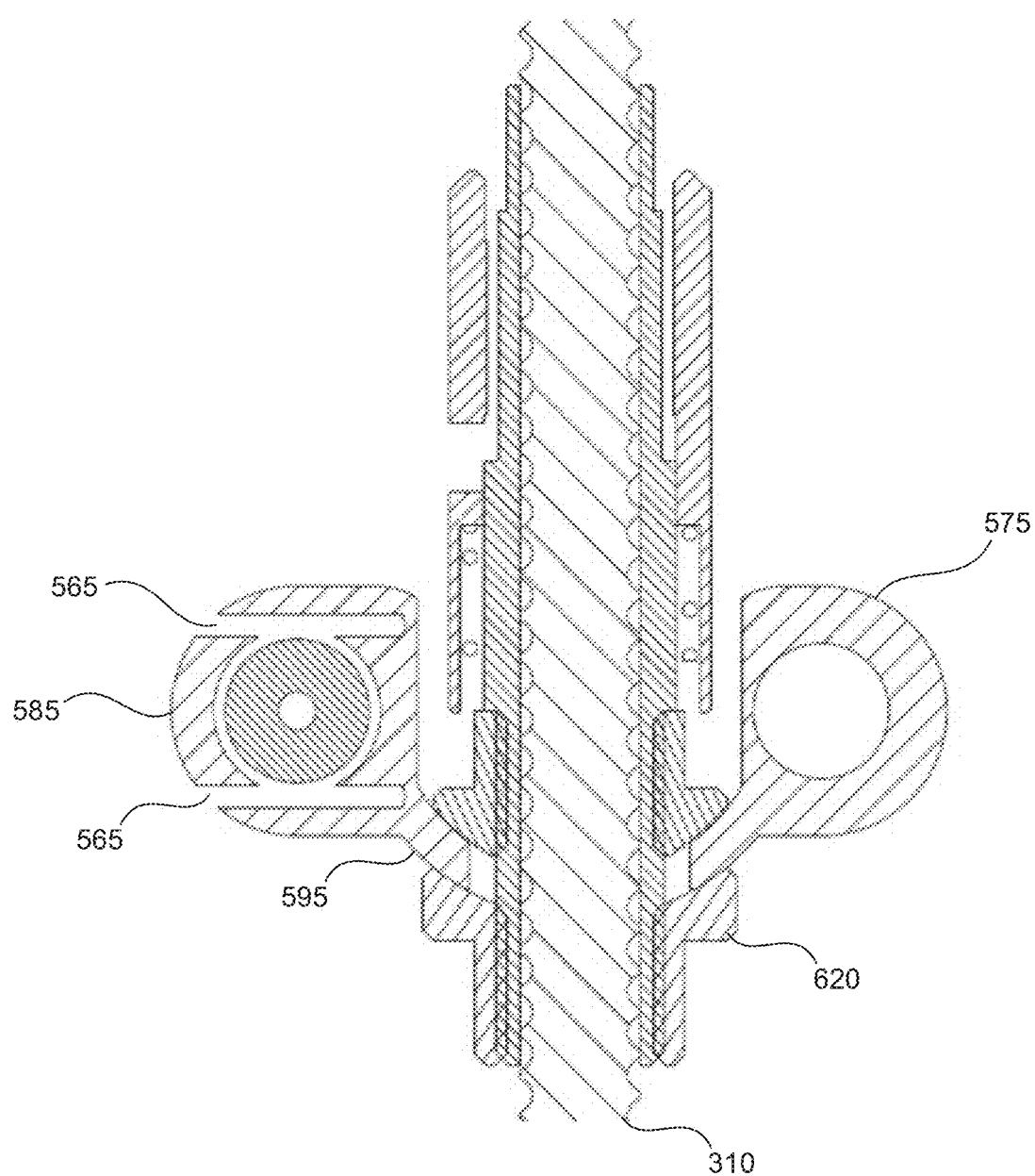
FIG. 14 is a vertical cross sectional view of the ring transport assembly of FIG. 12 at C-C.
Figure 15:
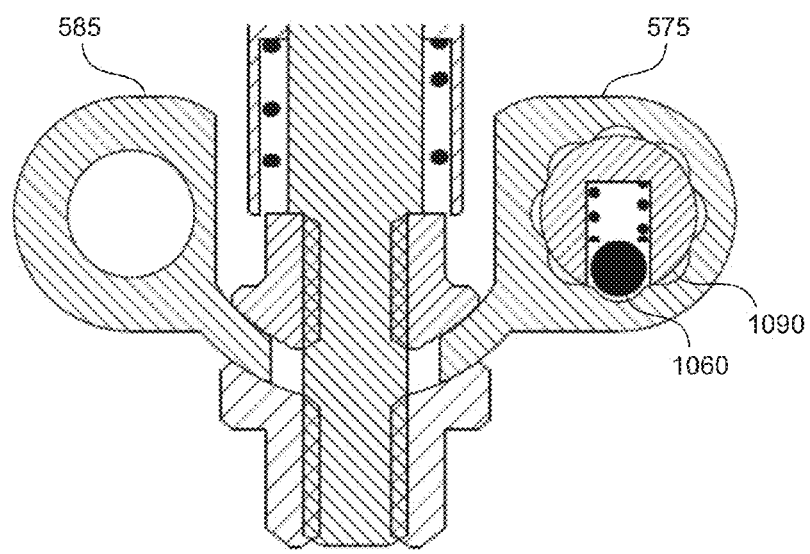
FIG. 15 is a vertical cross sectional view of the ring transport assembly of FIG. 12 at D-D.
Figure 16:
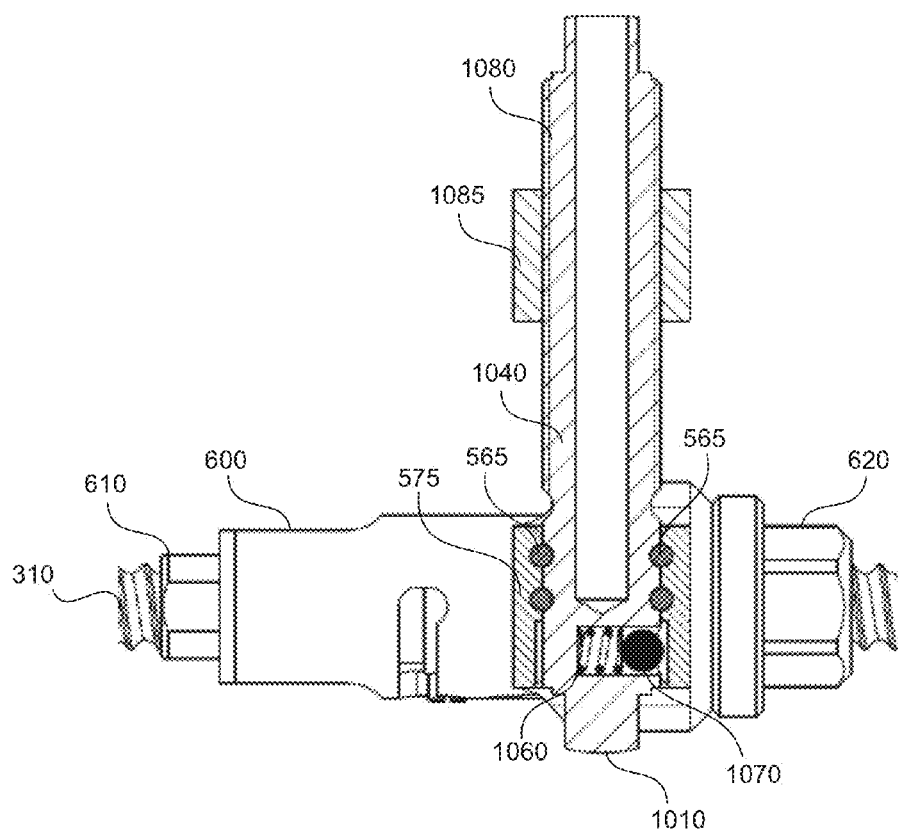
FIG. 16 is a vertical cross sectional view of the ring transport assembly of FIG. 12 at E-E.
Figure 17:
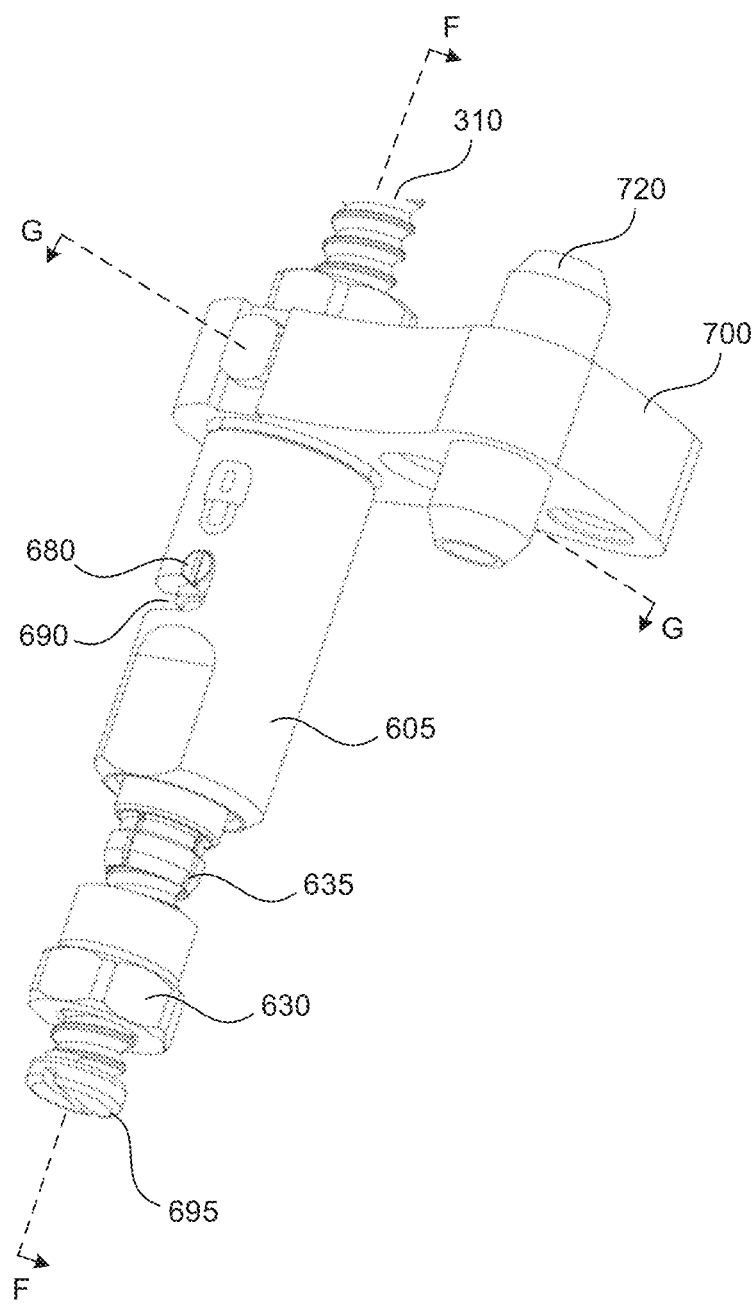
FIG. 17 is a perspective view of a quick release and frame height adjustment mechanism and flange in accordance with an embodiment of the present invention.
Figure 18:
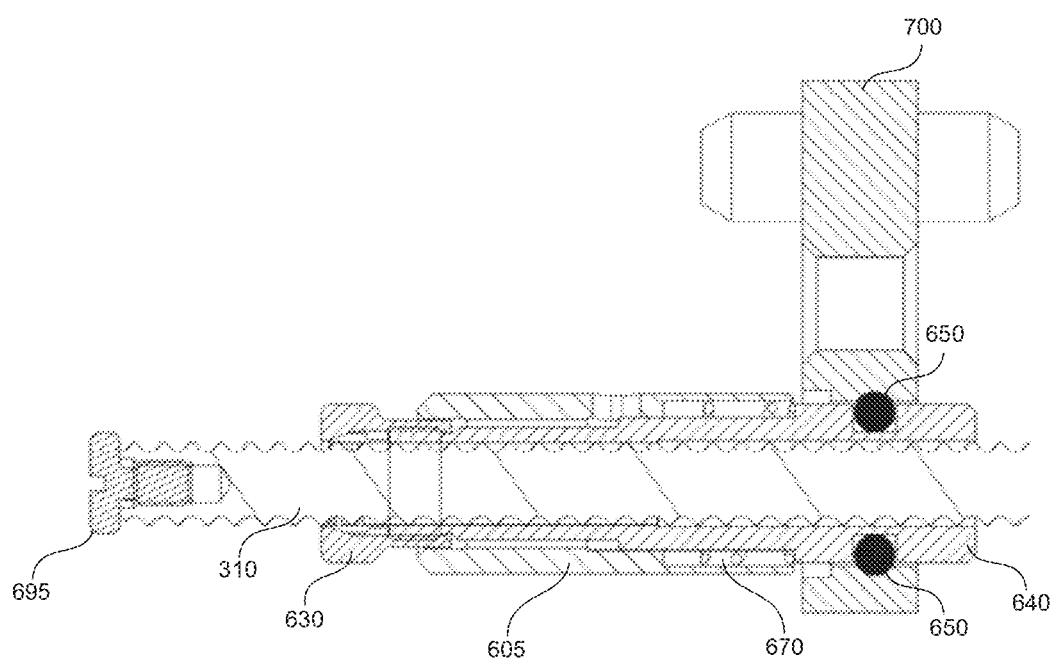
FIG. 18 is a vertical cross sectional view of the quick release and frame height adjustment mechanism and flange of FIG. 17 at F-F.
Figure 19:
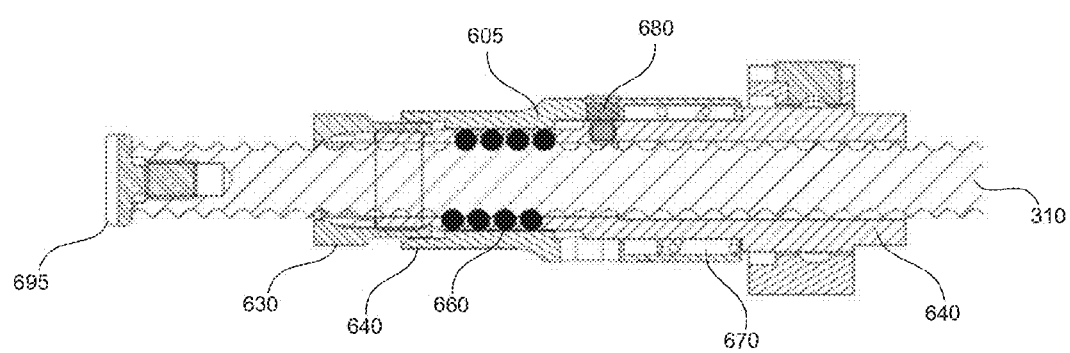
FIG. 19 is vertical cross sectional view of the quick release and frame height adjustment mechanism of FIG. 17 at G-G, which is orthogonal to section F-F.
Figure 20:
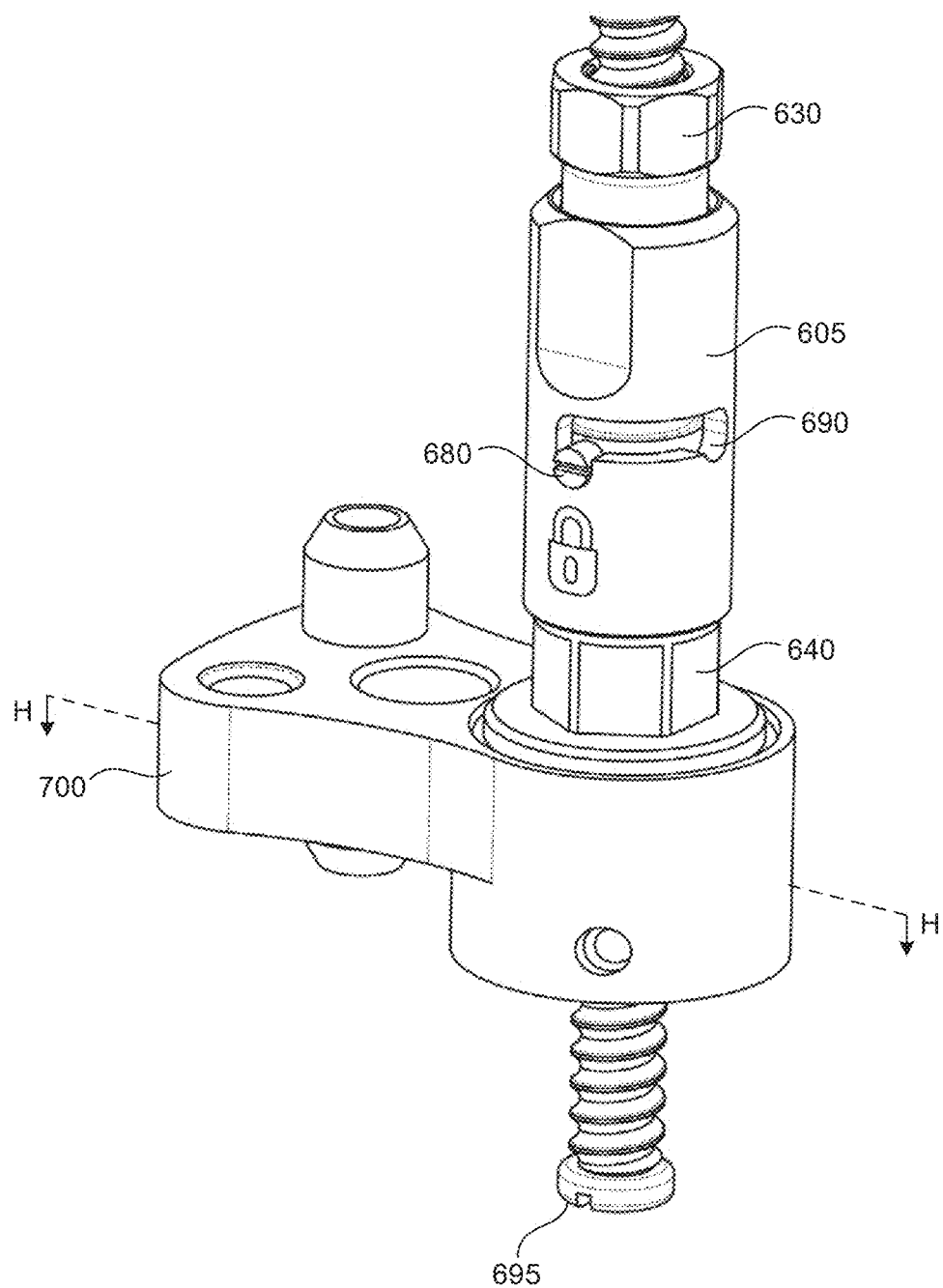
FIG. 20 is a perspective view of an alternate configuration of a quick release and frame height adjustment mechanism and flange of an embodiment of the present invention.
Figure 21:
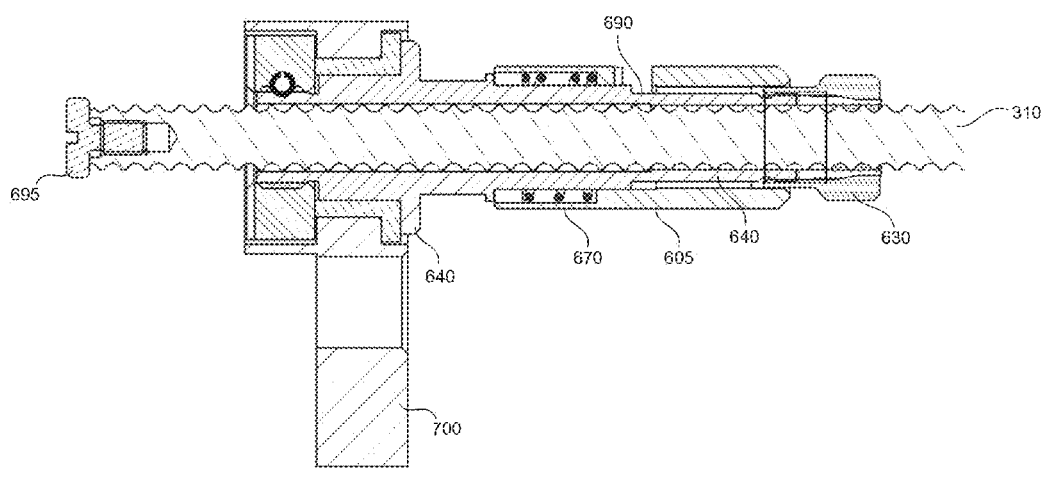
FIG. 21 is a vertical cross sectional view of the quick release and frame height adjustment mechanism and flange of FIG. 20 at H-H.

The flat surfaces of the flange 700 and the transport rings 200 allow the flange 700 to be coupled to the upper 285 or lower 280 ring surfaces of the transport rings 200 as seen in FIG. 10. This provides the user with the option of coupling a bone transport ring 200 to the top of flange 700 or to the bottom of flange 700. Also, the dimensions of the flange 700 allow the strut assembly 300 to be coupled to the bone transport ring 200 such that the strut 310 can lie either inside the bone transport ring 200 or outside of the bone transport ring 200 as seen in FIG. 11.

Referring to FIGS. 12-16, there are shown different illustrations of a bone transport assembly 150 of the first embodiment of the invention. The bone transport assembly generally includes a ball and socket joint 500, a quick release mechanism 600, and a translational rod 1000.

The ball and socket joint 500 has a hyperbolic collar 595 that fits loosely over the distal end of the quick release mechanism 600 and is coupled to the quick release mechanism 600 by a locking nut 620 that substantially conforms to the shape of the hyperbolic collar 595. When the locking nut 620 is loosened, the ball and socket joint 500 is free to swivel about a three dimensional axis until the locking nut 620 is tightened, thereby locking the ball and socket joint 500 at its latest position. This feature enables the medial ring 240 to rotate so that it is no longer parallel with the proximal 220 and distal 260 rings, thus allowing the second bone segment 840 to be more precisely aligned with the third bone segment 860 as the distraction osteogenesis process progresses. An example of a medial ring 240 being non-parallel to a proximal 220 and distal 260 ring is shown in FIG. 3, for example. The ball and socket joint 500 also helps in aligning second bone segment 840 with third bone segment 860 during the docking process. A user can accomplish this by unlocking locking nut 620, marginally loosening the ball and socket joint 500, and rotating at least one of the top click mechanism 400 and translational short rod 1000 or translation bolt 730.

The hyperbolic collar 595 terminates on two sides with a first retaining ring 575 on one side and a second retaining ring 585 on the opposing side. The first retaining ring 575 connects and retains the translational rod 1000 to the ball and socket joint 500 by way of a series of retaining pins 565. The second retaining ring 585 provides the user the option to add an extra rod of any type, for example, to provide extra stiffness to the frame 100, if desired.

The translational rod 1000 has a structure similar to the click mechanism 400. One end of the translational rod 1000 terminates in a square head 1010 that can mate with a driving tool such as a screw driver. The translational rod 1000 includes a driving body 1040 with a cylindrical notch 1070 that houses a spring and ball system 1060. A first retaining ring 575 includes recesses or profile cuts 1090. As the driving body 1040 is rotated, the ball of the spring and ball system 1060 may move from one profile cut 1090 and into an adjacent profile cut 1090.

The driving body 1040 is threadedly mated to a connector piece 1085. The connector piece 1085 includes an aperture 1095. The connector piece 1085 can be fixed to a bone transport ring 200 by means of a fastener, such as a locking nut 1097 that extends through a through-hole 210 of a bone transport ring 200 and further through the aperture 1095 of the connector piece 1085.

When the square head 1010 of the translational short rod 1000 is rotated, for example by a screw driver, the driving body 1040 rotates. As the driver body 1040 rotates, the spring and ball system 1060 provides feedback to the user each time the ball moves into one of the profile cuts 1090 of the first retaining ring 575. The rotation of the driver body 1040 forces the outer body 1080 to move axially. The axial movement of the outer body 1080 is caused by the inability of the outer body 1080 to rotate, due to the rigid connection to the connecting piece 1085 and the bone ring 200. The axial movement of the outer body 1080 causes the connector piece 1085 to move in conjunction with the outer body 1080. Finally, the movement of the connector piece 1085 moves the bone transport ring 200 to which the connector piece 1085 is attached, allowing translation of the bone transport ring 200 towards or away from strut assembly 300. This translation of the medial ring 240 may be useful when "docking" the bone. The docking phase is reached at the end of the transport phase, when the second bone segment 840 reaches the third bone segment 860. Sometimes the two bone segments do not align well and then it becomes advantageous to translate the medial ring 240 to correct the alignment between the second bone segment 840 and the third bone segment 860.

Quick release mechanism 600 of bone transport assembly 150 allows for quick adjustment of the medial ring 240 compared to the finer adjustment by the top click mechanism 400. It should be noted that the quick release mechanism 600 is only intended to be used prior to fixation of the bone transport frame 100 to the patient. Because the distal ring 260 includes an anti-torque quick release mechanism 605, which is substantially similar to the quick release mechanism 600, the workings of the quick release mechanism 600 are omitted here and are described with reference to the anti-torque quick release mechanism 605.

Referring to FIGS. 17-21, the distal portion of the strut assembly 300 generally includes a flange 700, an anti-torque quick release mechanism 605, and a tapered nut 630.

The anti-torque quick release mechanism 605 has an unlocked state, a semi-locked state, and a locked state. In the unlocked state, the anti-torque quick release mechanism 605, flange 700 and attached distal ring 260 are free to move vertically up or down the strut 310 regardless of rotation of the strut 310. This allows for quick adjustment of the distal ring 260 prior to fixing the bone transport frame 100 to the patient's bone. The quick release mechanism 600 provided with the medial ring 240 has the same feature.

In the semi-locked state, the anti-torque quick release mechanism 605 travels vertically up or down the strut 310 with rotation of the strut 310 by the top click mechanism 400. To switch from the unlocked state to the semi-locked state, the user rotates the anti-torque quick release mechanism 605. To accomplish this, the body of the anti-torque quick release mechanism 605 is pushed proximally, compressing spring 670. This moves locking pin 680 into a position in groove 690 which allows for rotation of the body of the anti-torque quick release mechanism 605. Rotation is continued until the locking pin 680 traverses to the opposite side of the groove, allowing the spring to decompress. Once rotated, the bearings 660 engage the thread of the strut 310, disabling the anti-torque quick release mechanism 605 from freely travelling vertically up or down the strut 310. Rather, it will move vertically up or down the strut 310 only with rotation of the strut 310 by virtue of rotation of the top click mechanism 400. It should be noted, however, that this function is only desirable for the quick release mechanism 600 coupled to the bone transport assembly 150, and not for the anti-torque quick release mechanism 605.

The anti-torque quick release mechanism 605 should only be configured in the unlocked state or the locked state, and not the semi-locked state. To switch from the semi-locked state to the locked state, the tapered nut 630 is threaded onto sleeve 640. Because of the taper inside tapered nut 630, the collet 635 at the tip of sleeve 640 bends inward and creates friction with the strut 310 when the tapered nut 630 is tightened. This friction causes the tapered nut 630, sleeve 640 and strut 310 to move as a single unit, rotating together with the strut 310. This rotation is possible because of the retaining balls 650, which allow these pieces to rotate inside the flange 700. The flange 700 is connected to the distal ring 260. Because there is no thread at the interface between the flange 700 and the combination tapered nut 630, sleeve 640 and strut 310, the distal ring 260 is not driven vertically up or down the strut 310 when it is rotated by actuation of the top click mechanism 400. The quick release mechanism 600, on the other hand, has no anti-torque feature and thus can only be in the unlocked or semi-locked state. When the quick release mechanism 600 is in the semi-locked state, the medial ring 240 thus can be driven vertically up or down the strut 310 allowing for transport.

The bearings 660, in addition to enabling the switch from the unlocked to the semi-locked positions, take much of the axial load when that load moves from the strut 310 to the sleeve 640 (e.g. when the patient is standing). The bent collet 635 alone may not be able to take all that axial loading. A screw 695 is provided at the far distal end of the strut 310 to prevent the anti-torque quick release mechanism 605 from sliding off the strut 310 when it is in the unlocked state and the distal ring 260 is being adjusted.

Figure 22:
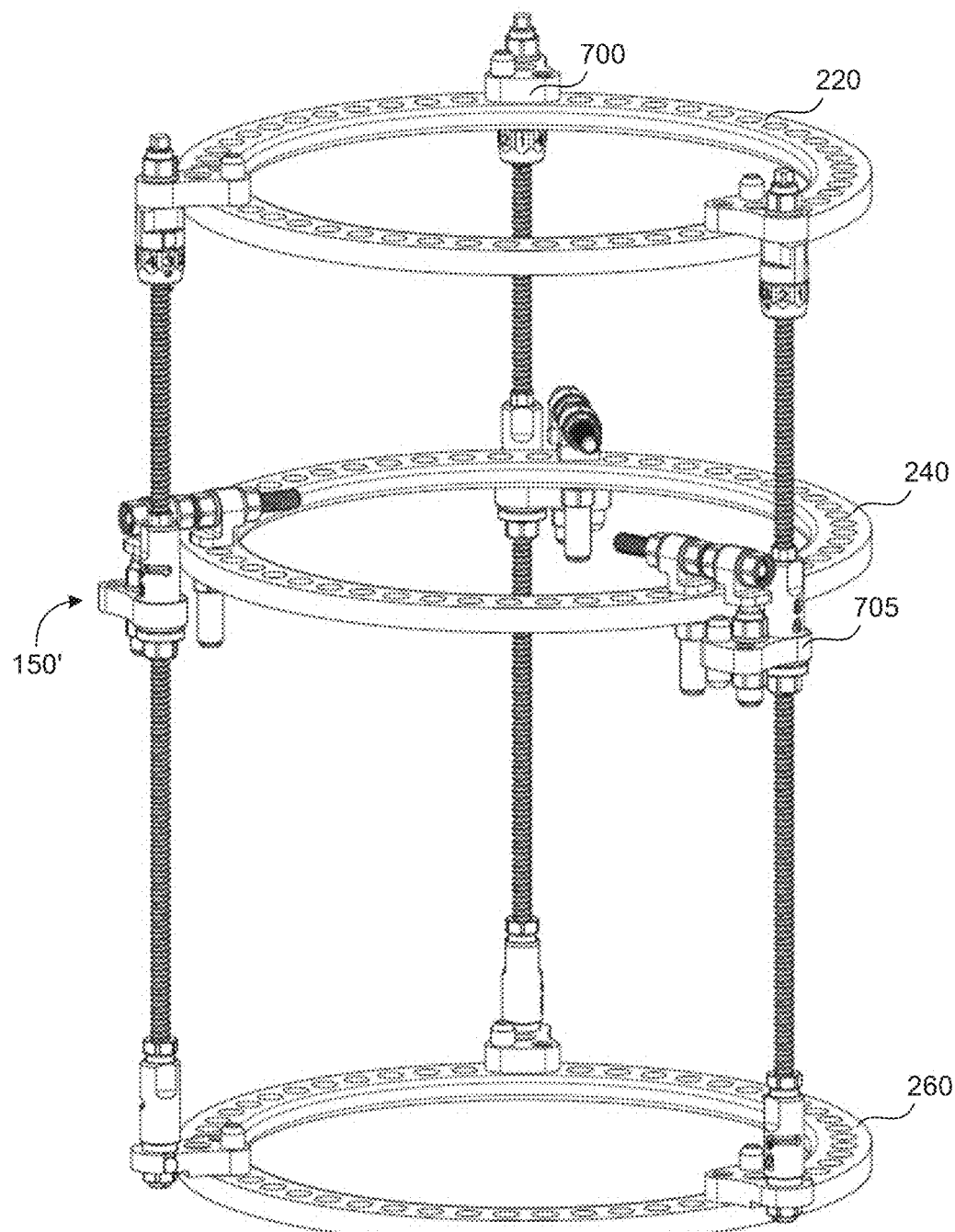
FIG. 22 is a perspective view of another embodiment of a bone transport frame in accordance with the present invention.
Figure 23:
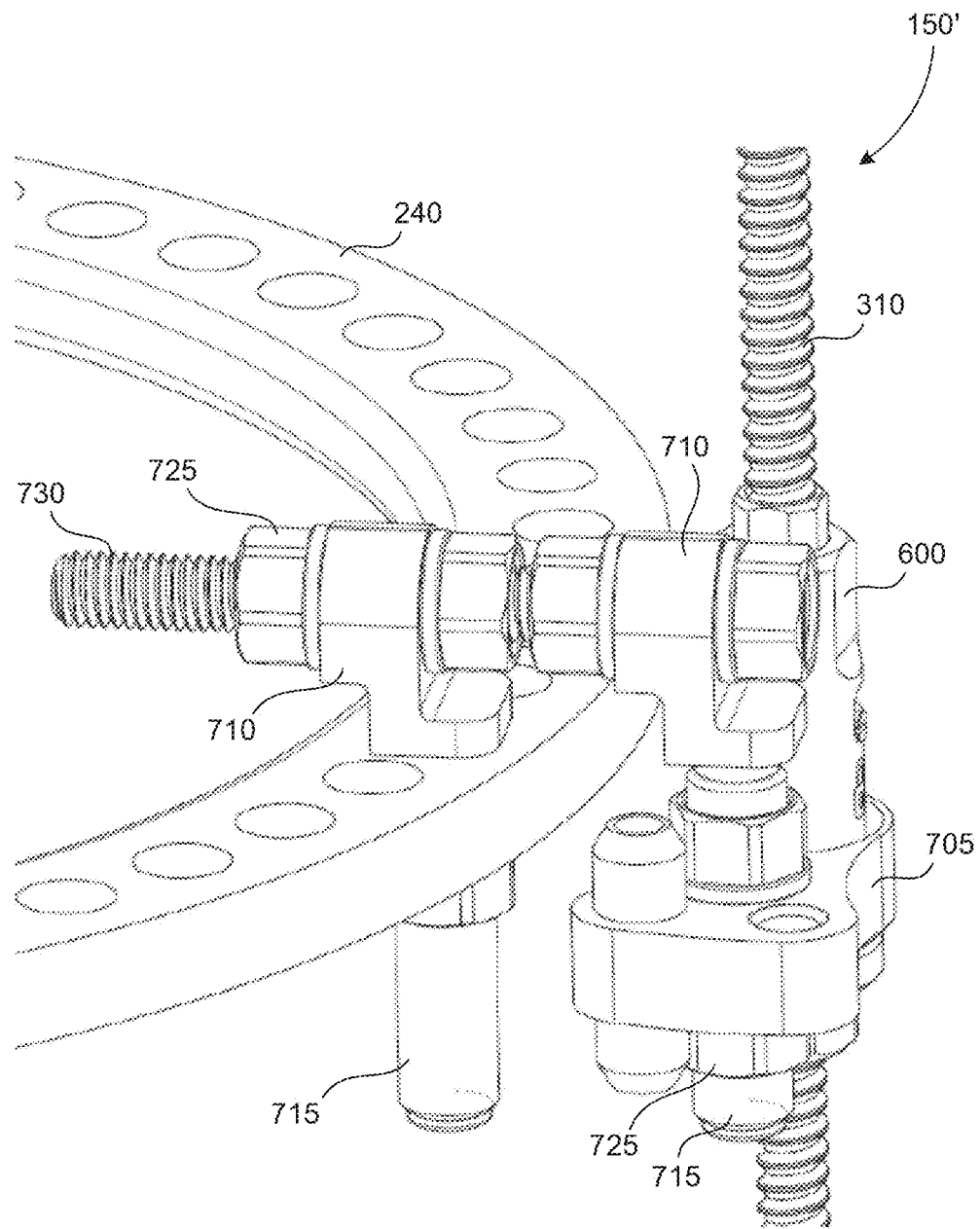
FIG. 23 is a perspective view of the bone transport assembly of FIG. 22.
Figure 24:
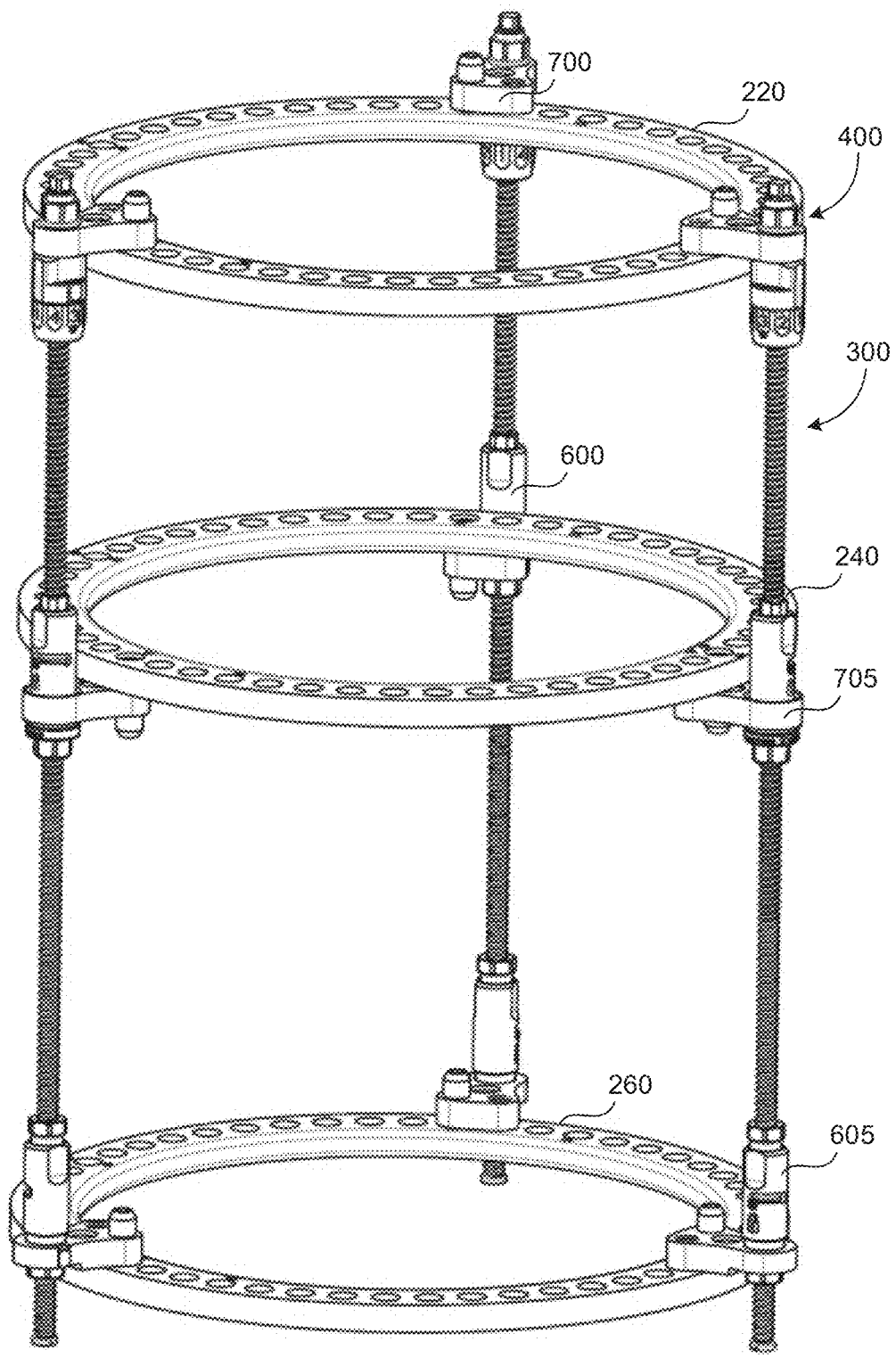
FIG. 24 is a perspective view of another embodiment of a bone transport frame in accordance with the present invention.
Figure 25:
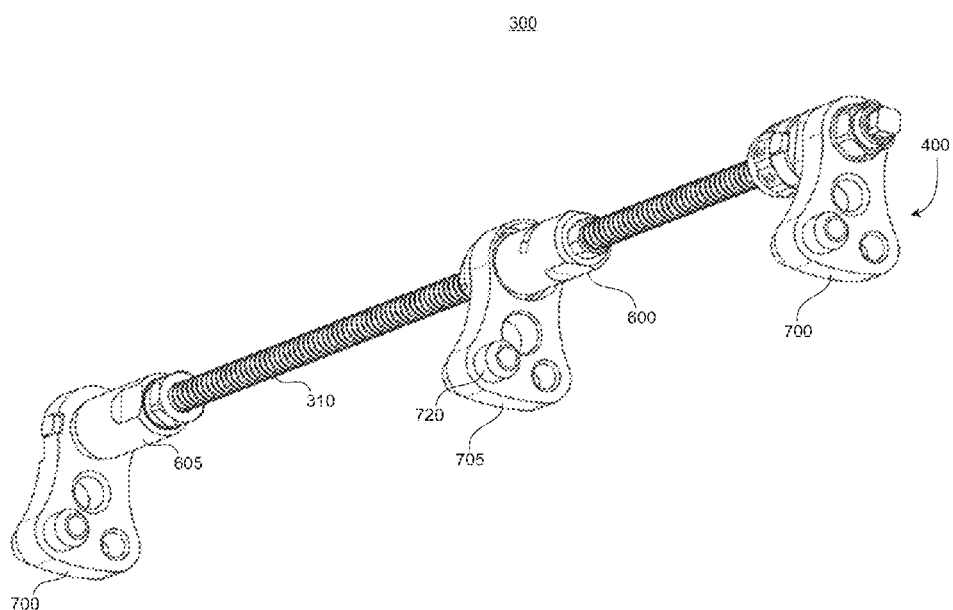
FIG. 25 is a perspective view of a strut assembly of the bone transport frame of FIG. 24.
Figure 26:
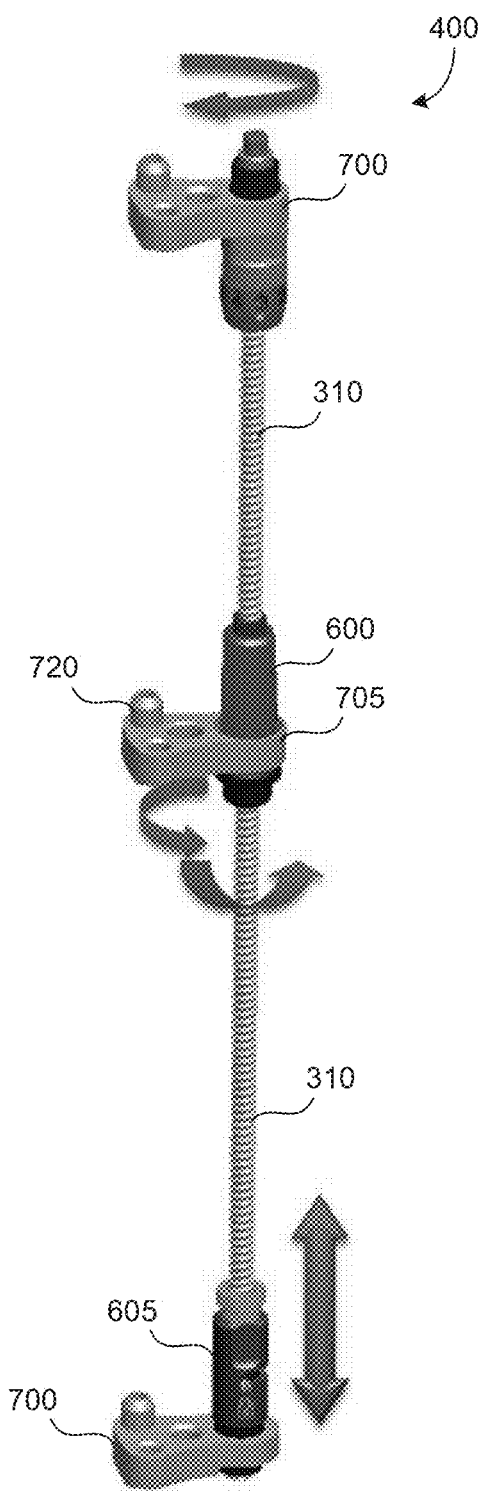
FIG. 26 is a perspective view illustrating possible movements of the bone strut assembly of FIG. 25.
Figure 27:
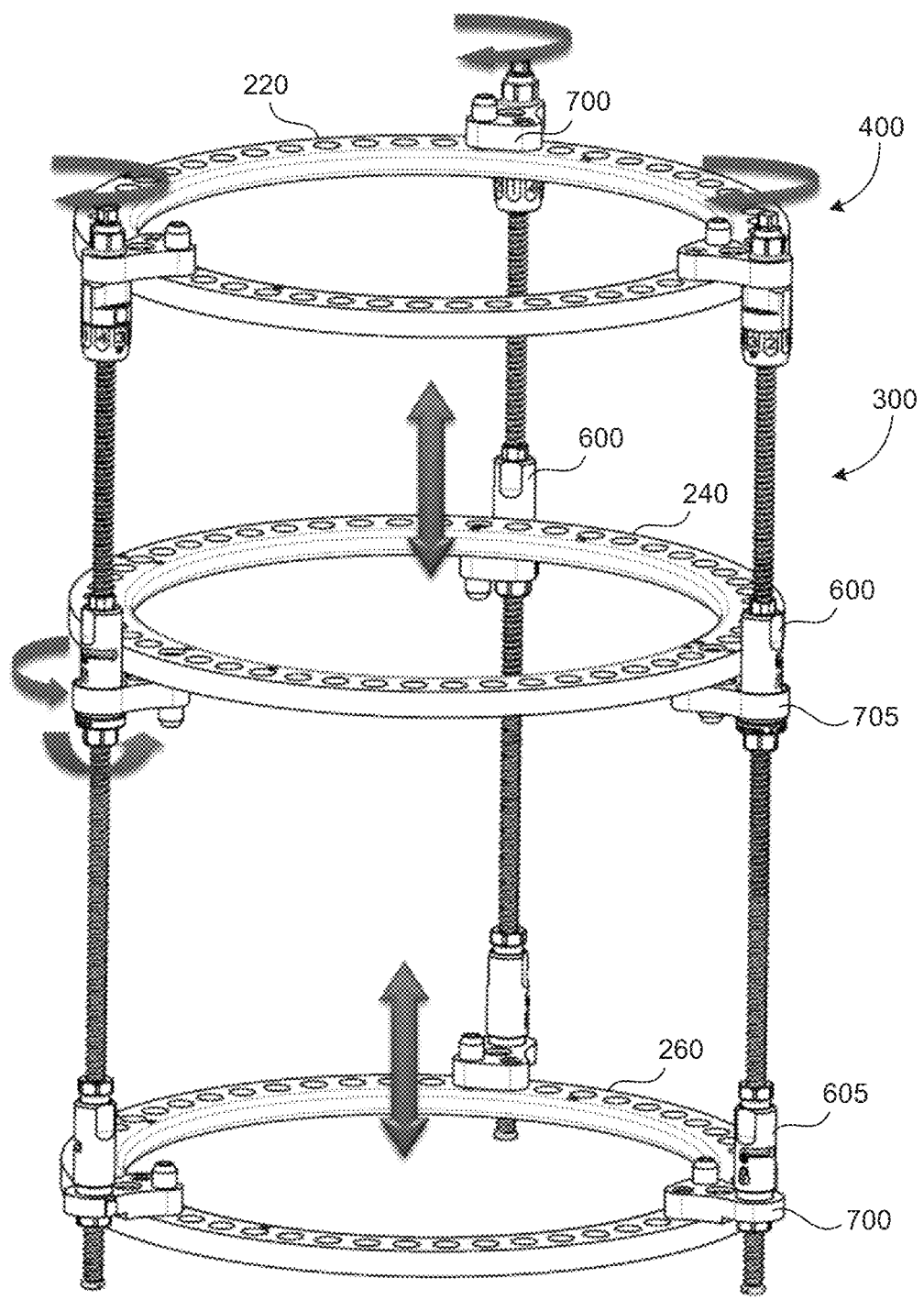
FIG. 27 is a perspective view illustrating possible movements of the bone transport frame of FIG. 24.

Referring to FIGS. 22-23, a second embodiment of a bone transport frame 100' is shown. The bone transport frame 100' generally includes a plurality of bone transport assemblies 150', a plurality of bone transport rings 200 and a plurality of strut assemblies 300.

One difference between the second embodiment shown in FIGS. 22-23 and the first embodiment shown in FIGS. 1-3 is that the bone transport assembly 150' coupled to the medial ring 240 includes a different structure such that the gradual translation of the medial ring 240 does not occur by way of a clicking mechanism.

The second embodiment of the bone transport assembly 150' comprises a quick release mechanism 600, a ball jointed flange 705, a series of hinge pin and bracket assemblies, a series of nuts, and a translational bolt.

The ball jointed flange 705 has a hyperbolic collar 595 much like the hyperbolic collar 595 seen on the ball joint 500 of the first embodiment. This ball jointed flange 705 is also coupled to the quick release mechanism 600 by means of the same locking nut 620. However, rather than terminating with a first retaining ring 575 and a second ring 585, the hyperbolic collar 595 terminates with a flange like that disclosed elsewhere herein. A hinge pin 715 is coupled to the ball jointed flange 705 through the medial through-hole 760 and is axially retained by a series of nuts 725, but is capable of rotation within the medial through-hole 760. The hinge pin 715 terminates at the proximal end with a bracket 710. Another hinge pin 715 and bracket 710 is coupled to a through-hole 210 of the medial ring 240. A translating bolt 730 connects both of the hinge pin 715 and bracket 710 assemblies and is retained by a series of nuts 725. The hinged connection in combination with the translating bolt 730 allows the surgeon to translate the medial ring 240 toward or away from the struts 310. This is accomplished by rotating the translating bolt 730. Furthermore, the ball jointed flange 705 allows for swivel about a three dimensional axis. These features combine to provide the medial ring 240 with six degrees of freedom.

Referring to FIGS. 24-28, there is shown a third embodiment of a bone transport frame 100". A difference between the bone transport frame 100" shown in FIGS. 24-28 and previous embodiments is that medial ring 240 does not have the capability of horizontal translation.

Figure 28:
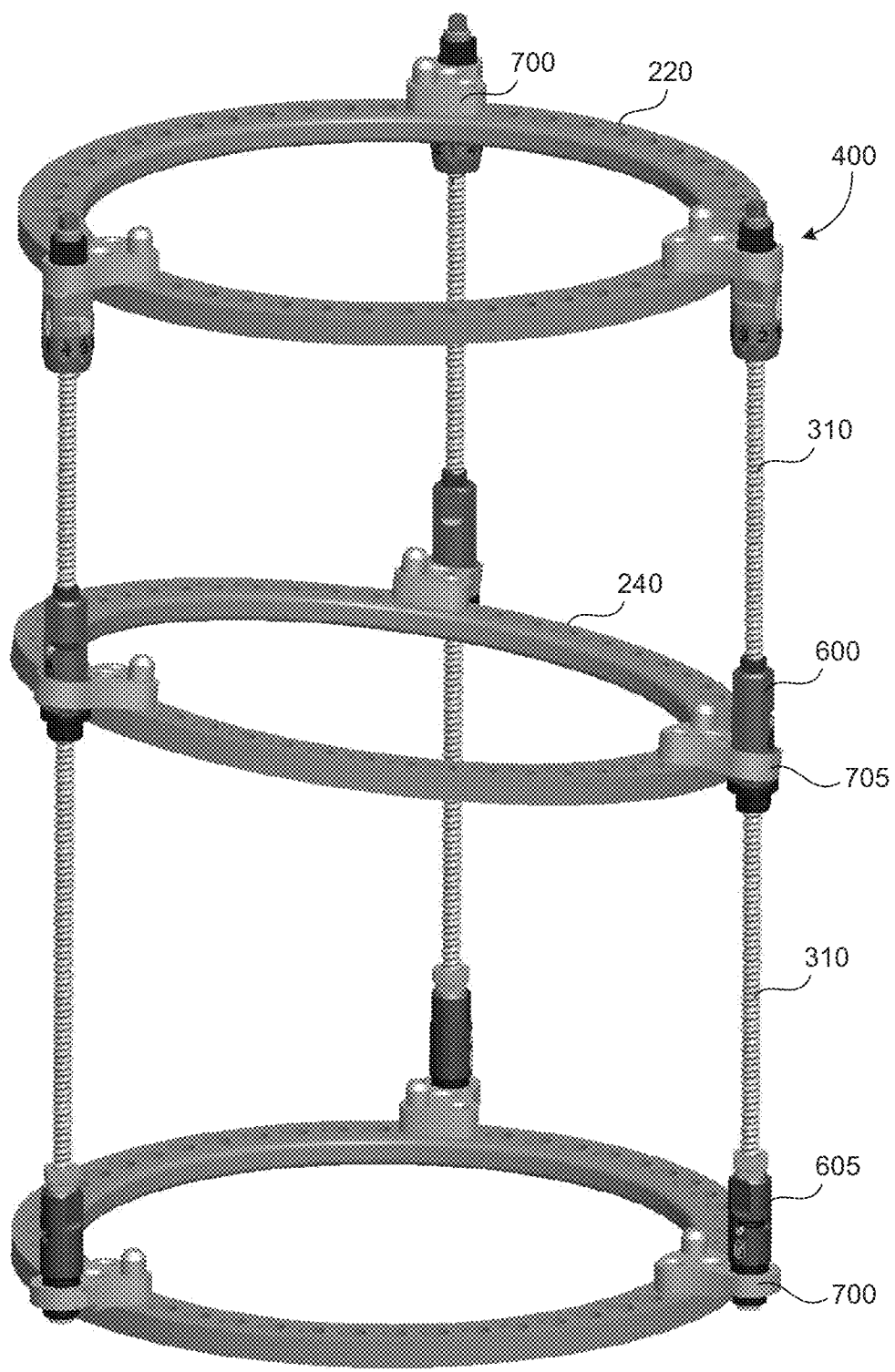
FIG. 28 is a perspective view of the bone transport frame of FIG. 24 illustrating the position of a medial ring after transport has occurred.

Structurally speaking, the embodiment shown in FIGS. 24-28 is obtained by taking the embodiment of the bone transport frame 100' shown in FIGS. 22-23, removing the translating bolt 730 and accessories, and directly attaching the ball jointed flange 705 to the medial ring 240. As disclosed elsewhere herein, the ball jointed flange 705 can connect to the medial ring 240 by virtue of a retaining pin 720 that extends through both a through-hole 210 of the medial ring 240 and through an anterior through-hole 740 of the ball jointed flange 705. This permits the medial ring 240 to move such that it is no longer parallel with proximal ring 220 and distal ring 260, but there are no mechanisms for translating medial ring 240 toward or away from the struts 310 as shown in FIG. 28.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone transport frame comprising:
    a first ring extending along a first plane and having a first longitudinal axis orthogonal to the first plane;
    a second ring extending along a second plane and having a second longitudinal axis orthogonal to the second plane;
    a plurality of elongate struts each having a longitudinal axis, the plurality of elongate struts having a parallel relationship to one another and being coupled to the first and second rings; and
    a plurality of ring transport assemblies each rotatably coupling the second ring to a respective one of the elongate struts so that the second longitudinal axis is rotatable from parallel to non-parallel with respect to the longitudinal axes of the plurality of elongate struts,
    wherein the parallel relationship of the plurality of elongate struts is fixed so that the elongate struts are adapted to remain in the fixed parallel relationship during adjustment of the second ring.

2. The bone transport frame of claim 1, further comprising:
    a third ring extending along a third plane and having a third longitudinal axis orthogonal to the third plane, the third ring being coupled to the plurality of elongate struts,
    wherein the second ring is positioned between the first ring and the third ring.

3. The bone transport frame of claim 1, wherein the first and second rings each include a plurality of through-holes that extend through upper and lower surfaces of the respective rings.

4. The bone transport frame of claim 3, further comprising a plurality of pin retention members and bone pins adapted to couple the first and second rings to a first bone fragment and a second bone fragment respectively.

5. The bone transport frame of claim 4, wherein each pin retention member is operatively coupled to a respective one of the through-holes of the first or second rings.

6. The bone transport frame of claim 4, further comprising a plurality of wire retention members and bone wires adapted to couple the first and second rings to the first and second bone fragments respectively.

7. The bone transport frame of claim 6, wherein each wire retention member is operatively coupled to a respective one of the through-holes of the first or second rings.

8. The bone transport frame of claim 1, further comprising:
    a plurality of flange extension members each coupling the first ring to a respective one of the elongate struts, each flange extension member including a first through-hole adapted to receive a first coupling member for coupling a first end of the flange extension member to the first ring and a second through-hole adapted to receive the respective elongate strut therethrough.

9. The bone transport frame of claim 8, wherein each flange extension member further includes a third through-hole adapted to receive a second coupling member for rigidly coupling the first end of the flange extension member to the first ring.

10. The bone transport frame of claim 1, further comprising a plurality of first adjustable members, each first adjustable member operatively coupled to a respective elongate strut, wherein activation of one of the first adjustable members transports at least a portion of the second ring in either a proximal or distal direction toward or away from the first ring.

11. The bone transport frame of claim 10, wherein the first adjustable member of each of elongate strut is located at the proximal end portion of the elongate strut.

12. The bone transport frame of claim 11, wherein the first adjustable member operatively coupled to each elongate strut is adapted to transport the portion of the second ring in the proximal or distal direction toward or away from the first ring an incremental distance.

13. The bone transport frame of claim 12, wherein the first adjustable member operatively coupled to each elongate strut is adapted to record each incremental distance adjustment.

14. The bone transport frame of claim 1, wherein each elongate strut further comprises:
    a threaded shaft and a position adjustment member coupled to a respective ring transport assembly, the position adjustment member adapted to transport along a length of the threaded shaft in the proximal and distal directions, the position adjustment member having a first position such that the location of the position adjustment member on the threaded shaft is constant when the threaded shaft is not being rotated in either clockwise or counterclockwise directions about the longitudinal axis of the elongate strut and a second position such that the location of the position adjustment member can transport in either the proximal or distal directions without the threaded shaft being rotated in either the clockwise or counterclockwise directions about the longitudinal axis of the elongate strut.

15. The bone transport frame of claim 14, wherein each ring transport assembly further comprises a locking member having a locked and unlocked state, and wherein when the locking member is in the unlocked state, the second ring is free to move such that the second longitudinal axis of the second ring is oblique to the longitudinal axis of the elongate strut.

16. The bone transport frame of claim 1, wherein at least one of ring transport assemblies comprises a flange and a ball joint, a first portion of the flange being coupled to the second ring and a second portion of the flange being coupled to the respective elongate strut, the ball joint enabling the second ring to rotate with respect to the first ring such that the second longitudinal of the second ring is oblique to the first longitudinal axis of the first ring.

17. The bone transport frame of claim 16, wherein the first portion of the flange is coupled to the second ring with a retaining pin extending through a through-hole of the second ring and a corresponding through-hole of the flange.

18. The bone transport frame of claim 16, wherein the first portion of the flange includes at least two through-holes and the second portion of the flange includes at least one through-hole.

* * * * *